United States Patent
Acharid et al.

(10) Patent No.: US 12,332,171 B2
(45) Date of Patent: Jun. 17, 2025

(54) DEVICE FOR SPECTROSCOPIC ANALYSIS OF A SAMPLE AND METHOD ANALYZING A SAMPLE BY MEANS OF SUCH A DEVICE

(71) Applicant: Spectralys Innovation, Asnières-sur-Seine (FR)

(72) Inventors: Abdelhaq Acharid, Luzarches (FR); Ines Birlouez, Ermont (FR); Papus Boutaouakou, Chessy (FR); Olivier Charles-Francois, Paris (FR); Elliot Legrand, Bagnolet (FR); Monji Messaoudi, Aubervilliers (FR); Stephane Oddos, Boulogne Billancourt (FR); Clement Voisin, Hermaville (FR)

(73) Assignee: SPECTRALYS INNOVATION, Asnières-sur-Seine (FR)

( * ) Notice: Subject to any disclaimer, the term of this patent is extended or adjusted under 35 U.S.C. 154(b) by 305 days.

(21) Appl. No.: 18/021,774

(22) PCT Filed: Aug. 20, 2021

(86) PCT No.: PCT/EP2021/073197
§ 371 (c)(1),
(2) Date: Feb. 16, 2023

(87) PCT Pub. No.: WO2022/038287
PCT Pub. Date: Feb. 24, 2022

(65) Prior Publication Data
US 2024/0027339 A1    Jan. 25, 2024

(30) Foreign Application Priority Data

Aug. 21, 2020 (FR) .................. FR2008613

(51) Int. Cl.
*G01N 21/3563* (2014.01)
*G01N 21/03* (2006.01)
(Continued)

(52) U.S. Cl.
CPC ....... *G01N 21/3563* (2013.01); *G01N 21/645* (2013.01); *G01N 33/10* (2013.01);
(Continued)

(58) Field of Classification Search
CPC ............. G01N 21/3563; G01N 21/645; G01N 2021/0339; G01N 2021/6482;
(Continued)

(56) References Cited

U.S. PATENT DOCUMENTS 5,208,649 A    5/1993  Cuppoletti
8,946,618 B2   2/2015  Kalitsis
(Continued)

FOREIGN PATENT DOCUMENTS

EP    1850117 A1    10/2007
FR    3047313 A1    8/2017
(Continued)

OTHER PUBLICATIONS

International Search Report and Written Opinion received for PCT Serial No. PCT/EP2021/073197, mailed Feb. 24, 2022, 15 pgs.

*Primary Examiner* — Dominic J Bologna
(74) *Attorney, Agent, or Firm* — Merchant & Gould P.C.

(57) ABSTRACT

A device is for analyzing a heterogeneous sample (S). The device includes a measurement module having a reservoir configured to accommodate the sample (S), a first infrared spectroscopy subassembly and a second fluorescence spectroscopy subassembly. The first subassembly includes a diffusing optical element which is positioned so as to allow the implementation of reliable infrared spectroscopy measurements with a high precision without degrading the fluorescence spectroscopy measurements which take place on the same sample. The device includes a processing module connected to the measurement module by a communication network and a processor configured to analyze the data obtained by infrared spectroscopy and fluorescence spectroscopy.

11 Claims, 12 Drawing Sheets

(51) Int. Cl.
*G01N 21/64* (2006.01)
*G01N 21/84* (2006.01)
*G01N 33/10* (2006.01)

(52) U.S. Cl.
CPC .............. *G01N 2021/0339* (2013.01); *G01N 2021/036* (2013.01); *G01N 2021/0367* (2013.01); *G01N 2021/6482* (2013.01); *G01N 2021/8466* (2013.01)

(58) Field of Classification Search
CPC ..... G01N 2021/8466; G01N 2021/036; G01N 2021/0367; G01N 33/10
See application file for complete search history.

(56) References Cited

U.S. PATENT DOCUMENTS

| | | | |
|---|---|---|---|
| 2015/0377787 A1* | 12/2015 | Zeng | A61B 5/0071 356/301 |
| 2019/0369013 A1* | 12/2019 | Birlouez-Aragon | G01N 21/35 |
| 2021/0123861 A1* | 4/2021 | Voisin | G01N 21/3563 |
| 2024/0027339 A1* | 1/2024 | Acharid | G01N 21/3563 |

FOREIGN PATENT DOCUMENTS

| | | |
|---|---|---|
| WO | 2019118800 A1 | 6/2019 |
| WO | 2020012029 A1 | 1/2020 |

* cited by examiner

DEVICE FOR SPECTROSCOPIC ANALYSIS OF A SAMPLE AND METHOD ANALYZING A SAMPLE BY MEANS OF SUCH A DEVICE

CROSS-REFERENCE TO RELATED APPLICATIONS

This application is a National Stage Application of PCT/EP2021/073197, filed 20 Aug. 2021, which claims benefit of Serial No. FR2008613, filed 21 Aug. 2020 in France, and which applications are incorporated herein by reference. To the extent appropriate, a claim of priority is made to each of the above disclosed applications.

TECHNICAL FIELD OF THE INVENTION

The invention relates to the technical field of spectroscopic analysis, and in particular, infrared spectroscopy analysis and fluorescence spectroscopy analysis. The coupling of these two technologies indeed makes it possible to provide complementary, even synergic information, on the same sample.

The invention relates to a device for analysing a sample. The invention further relates to a method for analysing a sample by means of such a device.

In the scope of the invention, the sample is more specifically a heterogenous sample which can be solid (grains, crushed biscuit or crisps, dough) or powdered (flour, milk powder). A heterogenous sample in the sense of the invention is a sample comprising elements of varied and very absorbent sizes. For example, the sample can contain impurities. That being said, in the case of a grain sample, the heterogeneity of the sample can also hold its grain size.

The invention has its application in the agribusiness industry, and in particular in the cereal or dairy industry. The invention indeed aims to allow the analysis of a sample at different stages of its development by the professionals in question. In the agribusiness industry, in particular cereal or dairy, the industrial procedures require a precise knowledge of the properties and of the quality indices of the samples analysed (Hagberg falling number of wheat, alveograph, farinograph, or also breadmaking tests on dough). As part of this, the analysis of samples by means of spectroscopic techniques makes it possible to extract, in a few tens of seconds, all the physicochemical information which is conveyed easily in various functionalities of the product, through the construction of calibrations between the spectral information and the criteria describing the functionalities.

TECHNICAL BACKGROUND

Spectroscopy devices having resorted to different analysis methods are known, making it possible to obtain physicochemical information about samples. The analysis methods in this regard are conventionally fluorescence spectroscopy and infrared spectroscopy.

Document WO 2019/118800 A1 discloses a measuring appliance available commercially which makes it possible to perform physicochemical analyses on samples by means of infrared spectroscopy and fluorescence spectroscopy measurements. The appliance comprises one single source and a monochromator making it possible to modify the wavelength of the beam emitted over a spectral range suitable for taking the two types of measurement. The appliance comprises a set of mirrors and reflectors making it possible for the beam emitted by the source to take various optical paths, at least one of which is dedicated to the infrared spectroscopy measurements and at least one other to the fluorescence spectroscopy measurements.

If this appliance actually makes it possible to take measurements on the same sample, the sample volume which can be analysed is 1 cm$^3$. Indeed, this type of appliance is mainly used in academic environments where the observed samples are homogenous model samples, often of a very small size. However, if this volume was expressed as a number of grains, while would only represent a few grains, and in addition, of a very small size. Yet, in the agribusiness industry, in particular cereal or dairy, the samples studied—grains, doughs, powders, etc.—are not only generally very heterogenous in terms of size, shape, even composition, but in addition, they have a lot greater volume, this such that they are representative of the content of a silo (several thousand cubic metres). Furthermore, if this appliance makes it possible to analyse not very absorbent samples such as liquid samples, thin layers, paper layers, precious stones, etc., it is not adapted to analyse very absorbent samples.

To measure the heterogenous sample parameters, such as defined above, with precision and complying with the industrial standards, adapted devices have been developed.

From document EP 1 850 117 A1, a spectroscopy analysis device is known, making it possible to take measurements on such samples from two types of measurements. The device comprises a first module dedicated to infrared spectroscopy analysis. This module comprises a chamber equipped with a source emitting an electromagnetic radiation in the near-infrared and infrared to illuminate the sample, a network monochromator-type detector or a filter serving to read the transmittance spectrum of the sample and a placement intended to accommodate said sample. The device further comprises a second module specifically dedicated to fluorescence spectroscopy analysis. This module comprises a chamber comprising a source emitting an electromagnetic radiation intended to illuminate the sample, such that the latter, under the effect of this radiation, emits a fluorescence-typical signal. The module also comprises a fluorescence detector capable of measuring the signal emitted by the sample and a placement reserved for the sample.

Two operating modes, each associated with a configuration are thus possible. In a first configuration, a material sample is separated beforehand into two samples, each being moved towards a specific module, with the aim of taking a type of measurement in particular, while in a second configuration, said material sample is successively moved from one module to the other.

When the sample is separated into two samples, additional manipulations are necessary to separate the sample. In addition, the sample volume analysed by infrared spectroscopy is never the same as the sample volume analysed by fluorescence spectroscopy, since the two samples are always distinct, all the same they come from the same starting sample, by the very fact of the heterogeneity of this starting sample.

When the sample is moved successively between the two modules of the appliance, additional manipulations are required to move the sample from one module to another. In addition, always according to this configuration, it is not possible to guarantee that a volume of the sample analysed by infrared spectroscopy is the same volume of an independent test sample which is analysed by fluorescence spectroscopy cover the same physicochemical reality, due to dispersion. Indeed, if the solid sample is of heterogenous nature, thus there is always a doubt that the subsample analysed is not representative of the initial sample, and even if the sample is representative of the initial sample, the positioning of the sample in the measuring chamber is not the same during the movement of the sample between the two modules. This will necessarily have an impact on the measurement.

The abovementioned spectroscopy analysis devices therefore suffer from several disadvantages, since either they do not make it possible to analyse heterogenous samples, of varied and very absorbent sizes, or they do not make it possible to take infrared spectroscopy and fluorescence spectroscopy measurements on the same sample, without having to move the sample or to separate the sample in two.

The consequence of this is that the devices of the prior art do not make it possible to perform an optimised coupling of the data obtained by infrared spectroscopy and by fluorescence spectroscopy, since the image of the sample measured by infrared spectroscopy does not correspond to the image of this sample measured by fluorescence spectroscopy.

SUMMARY OF THE INVENTION

The invention makes it possible to overcome the abovementioned disadvantages and proposes, to this end, a device for analysing a heterogenous sample, said device being characterised in that it comprises:
 a measuring module comprising:
  a reservoir configured to accommodation said sample and equipped with a first wall and a second wall opposite the first wall,
  a first infrared spectroscopy subassembly comprising a first excitation source configured to emit an electromagnetic radiation in the infrared field and/or of the near-infrared field to the first wall of the reservoir, said first wall being transparent for the infrared electromagnetic radiation, and a first means for acquiring transmittance spectra,
  a second fluorescence spectroscopy subassembly comprising at least one second excitation source configured to emit an electromagnetic radiation in the ultraviolet and/or visible field to the second wall of the reservoir, said second wall being transparent for the electromagnetic radiations, such that the volume of the sample which can be illuminated by the first excitation source corresponds to at least partially the volume of the sample which can be illuminated by the second excitation source, and a second means for acquiring fluorescence spectra of said sample,
  the first subassembly comprising a diffusing and transparent optical element for the electromagnetic radiation emitted by said first excitation source, said optical element being positioned between the first excitation source and the first wall of the reservoir or between the second wall of the reservoir and the first acquisition means, outside of an optical path of the electromagnetic radiation emitted by the second excitation source and outside of a solid angle for collecting a fluorescence signal emitted by the sample when it is exposed to electromagnetic radiation emitted by the second excitation source, and
 a processing module connected to the measuring module by a communication network and comprising a processor configured to analyse the data obtained by infrared spectroscopy and fluorescence spectroscopy.

Thus, a device is disposed, making it possible to analyse solid or powdered heterogenous samples, of varied sizes and very absorbent such as grains, flours, doughs, etc. In addition, the device makes it possible to implement infrared spectroscopy and fluorescence spectroscopy measurements in one single module without having to move the sample to be analysed from one module to another or to separate it in two to take two types of measurements. In such a configuration, the volume of the sample analysed by infrared spectroscopy always corresponds at least partially to the volume of the sample analysed by fluorescence spectroscopy, which makes it possible to correlate the data coming from the two types of measurements. In addition, the number of manipulations is reduced, which makes it possible to reduce the impact over time of the measurements and the time spent to take the measurements. This makes the device according to the invention, a device which is particularly suitable for physicochemical analysis in an industrial environment.

The problem linked to measuring the transmittance of very absorbent samples has been resolved by resorting to the diffusing and transparent optical element.

Conventionally, when it is sought to take infrared spectroscopy measurements (transmittance and/or reflectance) on heterogenous samples, of varied sizes and very absorbent, there is such a difference in light intensity transmitted between the measurement without sample and the measurement with the sample that the intensity ratio between the measurement without sample and the measurement with sample is around 20000. To correct this problem, there are two natural solutions. The first consists of adding an absorbent element on the optical path between the source and the detection means during the measurement without sample. The absorbent element makes it possible to obtain intensities which are comparable with and without the sample, but alters the optical path between the two measurements. An additional "component" must therefore be considered in the spectra obtained and possibly removed, which can prove to be complex. The second solution consists of altering, i.e. attenuating, the spectrum of the source itself by making the light intensity vary between the two measurements. The problem which is thus posed is that of repeatability of the measurements.

The diffusing and transparent optical element makes it possible to make the radiation emitted by the source diffuse during the infrared spectroscopy measurement without sample and therefore makes it possible to reduce the intensity of the light transmitted to the detector during this measurement. However, during the measurement with the sample, as it makes the radiation emitted by the source diffuse, but in a lesser measurement than the heterogenous sample itself, due to the presence of elements of varied sizes and very absorbent, it constitutes a neutral and passive element, since it hardly attenuates the radiation of the source compared with the attenuation due to the sample itself, without loss of information. Thus, it is possible to significantly reduce the intensity ratio between the two measurements without extending the measuring time, without extending the length of the optical path, without adding any element to the excitation source and/or altering the optical spectrum of the excitation source. Thus, with respect to certain solutions of the prior art, the invention makes it possible to improve the repeatability of the measurements, provides more robustness and makes it possible to avoid having to modify the source between two measurements.

However, the integration of such an optical element diffusing in the single measuring chamber of the device, even though fluorescence measurements must also be taken on the same sample, which are by nature, very sensitive to diffusion, is far from being obvious. To respond to this problem, the diffusing optical element is positioned between the first excitation source and the first wall of the reservoir or between the second wall of the reservoir and the first acquisition means, outside of an optical path of the electromagnetic radiation emitted by the second excitation source and outside of a solid angle for collecting a fluorescence signal emitted by the sample when electromagnetic radiation emitted by the second excitation source is exposed. By being thus positioned, it is possible to take infrared spectroscopy measurements on heterogenous samples, of varied sizes and very absorbent, without impeding the fluorescence spectroscopy measurements. The device thus claimed therefore makes it possible to take reliable infrared spectroscopy and fluorescence spectroscopy measurements and with a high precision on the same sample.

The device of the invention makes it possible to improve the conformity between the image of the sample measured by infrared spectroscopy and the image of the sample measured by fluorescence spectroscopy and thus makes it possible to optimise the coupling of the data obtained by infrared spectroscopy and by fluorescence spectroscopy.

According to different features of the invention which can be taken together or separately:
- the optical element constitutes the first wall of said reservoir,
- the optical element is positioned between the first excitation source and the first wall of the reservoir, on the optical path between the first excitation source and the first acquisition means,
- the first wall of the reservoir is movable along an axis orthogonal to a plan passing through the first wall,
- the second wall of the reservoir is anti-reflective for the electromagnetic radiation emitted by the second source,
- said second excitation source is located between the second wall and the first acquisition means,
- an axis passing through the second acquisition means and a median plane and substantially orthogonal to the second wall of the reservoir forms an angle α with respect to an axis passing through the first excitation source and the second acquisition means,
- the first excitation source consists of a high-power halogen incandescence source,
- the second excitation source(s) emit(s) a monochromatic electromagnetic radiation,
- said second source(s) consist(s) of one (or more) LEDs,
- the device comprises a housing receiving a sample retaining system, said housing comprising inner faces on which the retaining system is flattened,
- the device comprises a sample retaining system, comprising:
  - the reservoir, said reservoir comprising a first glazed part equipped with the first wall and a second glazed part equipped with the second wall, said first glazed part being removably mounted on said second glazed part,
  - a support block comprising a connection portion and a base for positioning the retaining system forming a bend with the connection portion in the device,
  - a removable portion comprising a housing receiving the reservoir, said second glazed part being fixed to the removable portion, said removable portion being removably connected with respect to the connection portion,
  - an articulated portion comprising an opening, said articulated portion being mounted pivoting on the support portion and capable of passing a mounting position wherein it is away from the removable portion at a use position, wherein it is folded down on the removable portion, said opening being opposite the reservoir, said articulated portion comprising compressible means making it possible to flatten the retaining system against the inner faces of said housing of the module receiving the retaining system when said articulated portion is in the use position.

The invention further relates to a method for analysing a sample by means of a device such as described above, said method comprising the following steps:
A) acquiring a transmittance spectrum of said sample with the first infrared spectroscopy subassembly,
B) acquiring fluorescence spectra of said sample with the second fluorescence spectroscopy assembly,
C) analysing the data obtained by infrared spectroscopy and fluorescence spectroscopy by means of the processing module, a processor being configured to determine at least one criterion characterising said sample from data coming from the analysis,
D) coupling the data obtained by infrared spectroscopy and fluorescence spectroscopy, at the spectral level, by means of the processing module, by concatenation of the spectra, processed beforehand, and by association of scores coming from the breakdown of each spectrum, to construct linear regressions or non-linear models and obtain calibrations of a descriptive criterion of the state of the sample, like a technological, sensorial or nutritional and sanitary quality criterion.

BRIEF DESCRIPTION OF THE FIGURES

Other aims and features of the invention will appear more clearly in the following description, made in reference to the accompanying figures, wherein.

DETAILED DESCRIPTION OF THE INVENTION

Figure 1A:
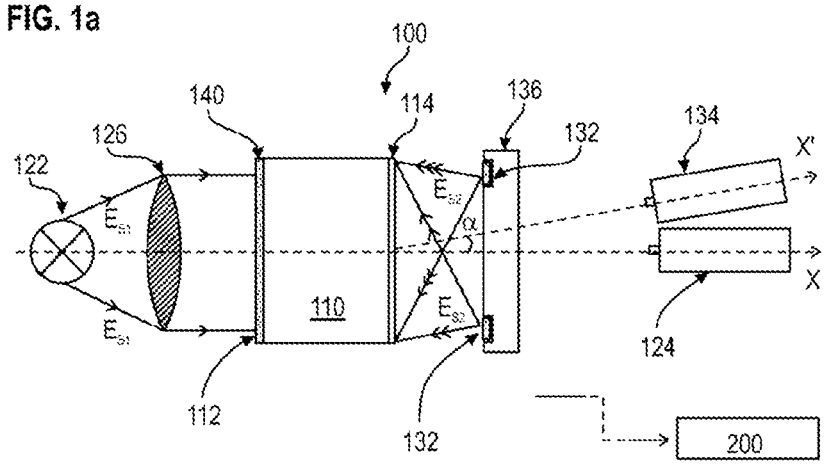
FIG. 1a is a schematic representation of an analysis device according to a first embodiment of the invention, wherein the optical element is positioned between the first excitation source and the first wall of the reservoir, the optical element forming part of the reservoir.

In reference to FIG. 1a, the invention relates to a device 1 for analysing a sample S comprising a measurement module 100 and a processing module 200 connected to the measurement module 100.

The measurement module 100 comprises a reservoir 110 to accommodate the sample S, a first infrared spectroscopy subassembly 120 and a second fluorescence spectroscopy subassembly 130.

Although the first infrared spectroscopy subassembly 120 and the second fluorescence spectroscopy subassembly 130 differ by the elements which compose them, their elements are however localised in a common module. Thus, contrary to known systems, the first subassembly 120 and the second subassembly 130 do not form submodules spatially delimited from one another, such as two boxes simply juxtaposed, but subassemblies of which the elements are arranged optimally in the single measurement module 100.

As will be seen in detail below, this optimal arrangement makes it possible to take infrared spectroscopy and fluorescence spectroscopy measurements by means of the first subassembly 120 and of the second subassembly 130 respectively without having to move or separate the sample, which makes it possible to reduce the number of manipulations, to perform an analysis on strictly the same sample and also to improve the repeatability of the measurements. Furthermore, the timeframe for taking the two measurements on the same sample is established as barely more than one minute, which allows the manufacturer to be able to deduce from it, the quantitative criteria of the grains in a short time, which can be qualified in real time. As will be better described below, the arrangement of the reservoir 110 and of the elements of the first and second subassemblies 120, 130 within the measurement module 100 according to the invention is particularly ingenious, since it makes it possible to take infrared spectroscopy and fluorescence spectroscopy measurements in a reduced time, by means of the single measurement module 100 and on one same sample S.

The reservoir 110 for accommodating the sample is equipped with a first wall 112 and a second wall 114 opposite the first wall 112.

The reservoir 110 can be of any shape, as long as it comprises a first and a second wall 112, 114 such as defined above. For example, the reservoir 110 can be of parallelepiped shape. In this case, the first and second walls 112, 114 can thus be formed at the level of two opposite faces of the parallelepiped. The reservoir 110 can also be of cylindrical shape. In this case, the first and second walls 112, 114 thus correspond to the bases of the cylinder. These are non-limiting examples.

The reservoir 110 advantageously delimits a volume intended to accommodate a sample S. The volume of the reservoir 110 is advantageously of around 100 mL. Furthermore, each of said first and second walls 112, 114 confers an illumination surface of a few tens of $cm^2$, preferably of around 20 $cm^2$, of cereal grains. What is important, is that the illuminated surface makes it possible to take a measurement representative of the sample, despite its heterogeneity while making it possible to have a suitable measuring time (around 1 minute) and a suitable device size (limited bulk). Thus, using several subsamples of a smaller size is avoided, which not only cannot be sufficiently representative of the batch analysed, but also which require a greater measuring and analysing time, etc. The dimensions of the reservoir are thus sufficient for investigating a quantity of material representative of all of the product, of which the manufacturer wants to know the properties from infrared spectroscopy and fluorescence spectroscopy measurements. The dimensions of the reservoir 110 are also suitable for taking both measurement by the two types of spectroscopy without unduly increasing the length of the optical path between the sources and the detectors of the first and second subassemblies 120, 130. Beyond these considerations, the reservoir 110 can have any dimension that the user of the device will deem suitable for the samples that they want to analyse.

Preferably, the reservoir 110 can also be equipped with a movable wall making it possible to adapt the volume of said reservoir according to the type of heterogenous sample (granular, powdered or doughy). The movable wall can be any of the walls of the reservoir 110. Thus, it is possible to reduce/increase the depth of the reservoir, which determines the optical path of the light beam, according to which small/large size grains are analysed, which have absorbance levels of the light inversely proportional to their size. If this is the first wall 112 of the reservoir, said first all 112 is thus, preferably, movable along an axis X1 orthogonal to a plane P1 passing through said first wall 112. According to the example of an embodiment illustrated in FIG. 1a, the first wall 112 extends along a substantially vertical plane P1. Thus, the axis along which the movable wall 112 moves is a horizontal axis.

Figure 4A:
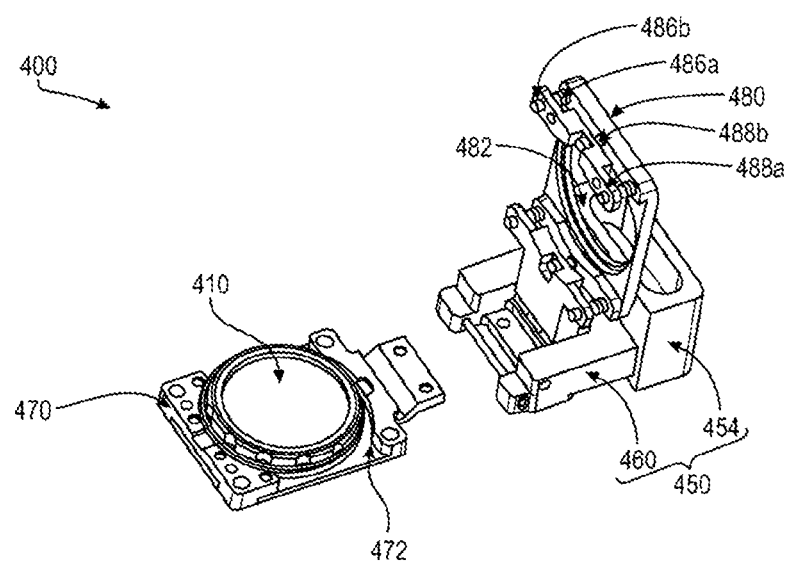
FIG. 4a is an illustration, in perspective, of a system for retaining a powdered, viscous or doughy sample for the device for analysing a sample according to the invention.
Figure 4B:
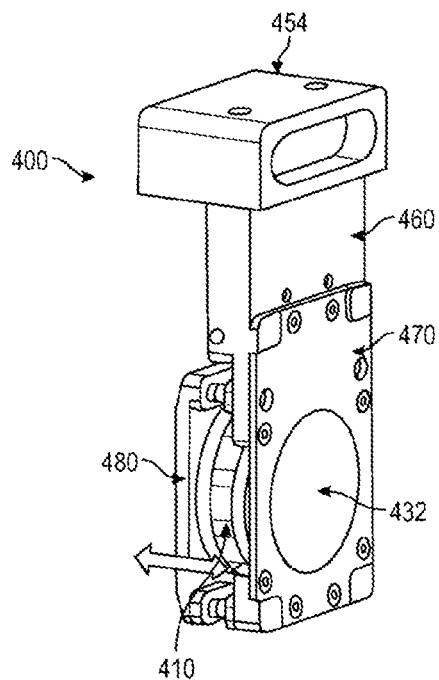
FIG. 4b is an illustration, in perspective, of the retaining system of FIG. 4, showing one of the faces of the retaining system.
Figure 5:
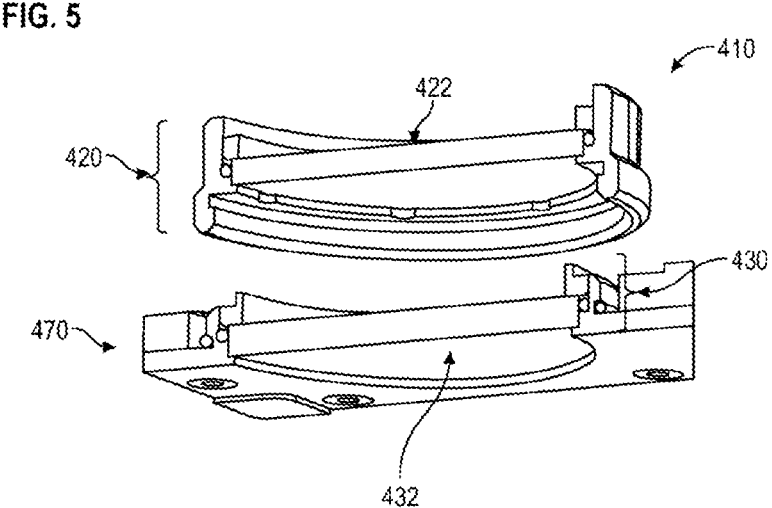
FIG. 5 illustrates a close and exploded view of the reservoir of the retaining system illustrated in FIGS. 4a and 4b.

According to a particular implementation of the device according to the invention illustrated in FIGS. 4a and 4b and 5, the analysis device 1 comprises a system 400 for retaining the sample configured to accommodate and dose as many granular, powdered samples as doughy samples.

The retaining system 400 comprises a reservoir 410 to accommodate the sample, which can be better seen in FIG. 5. The reservoir 410 comprises a first glazed part 420 equipped with a first wall 422. It further comprises a second glazed part 430 equipped with a second wall 432. It is specified that the term "glazed" is not at all limiting in the scope of the present invention, and that it does not involve any material from which the transparent walls are made, is necessarily glass. Indeed, this can be any other material as long as it has the same properties as the walls 122, 132 described above. The second wall 432 is separated from the first glazed part 420, an empty volume intended to accommodate the sample. The first glazed part 420 is removably mounted on said second glazed part 430, i.e. that the first glazed part 420 can be dismounted from the second glazed part 430.

The retaining system 400 further comprises a support block 450, a removable portion 470 and an articulated portion 480.

The support block 450 makes it possible to position the retaining system 400 in the measurement module 100 and, in particular, to adjust the height position of the reservoir 410. It comprises a connection portion 460 and a base 454 forming an angle/bend with the connection portion 460, which makes it possible to facilitate gripping by the user.

At the insertion of the retaining system 400 in the module 100, the gripping base 454 abuts with the module 100, allowing the connection portion 460 and the removable portion 470 to extend into the module 100. The connection portion 460 thus itself allows the removable portion to be suitably positioned in the module 100 to take measurements.

The retaining system 400 can be positioned in a housing provided for this purpose in the measurement module 100, on the optical path, the base 454 could thus serve as abutment. Alternatively, the retaining system 400 can be positioned at the level of an opening 150 illustrated in FIGS. 2a, 2b, serving to distribute the sample S. The retaining system 400 thus serves also as a blocker to prevent the outside light entering into the measurement module 100. In this configuration, the retaining system 400 appears suspended upside down, as illustrated in FIG. 4b, the base 454 and the connection portion being arranged in the opening 150 to prevent any uncoupling from the retaining system 400. When the retaining system 400 is not positioned in this place, a cover can be used as a blocker of the opening 150 during measurements.

The removable portion 470 comprises a housing 472 receiving the reservoir 410. Said removable portion 470 is connected, preferably removably, to said connection portion 460. In FIG. 4a, the removable portion 470 is illustrated in the dismounted position, while in FIG. 4b, it is illustrated in the mounted position. The second glazed part 430 is fixed to the removable portion 470 by being immovable in said removable portion.

The articulated portion 480 comprises an opening or orifice 482. The articulated portion is mounted pivoting on the support block 450. When it pivots with respect to the support block 450, the articulated portion is capable of moving from a mounting position wherein it is away from the removable portion 470 to a use position wherein it is folded down on the removable portion 470 (FIG. 4b). When the articulated portion 480 is in the use position, the opening 482 is opposite the reservoir 410, which makes it possible to not impede the passage of the electromagnetic beam arriving on this side of the reservoir 410, in this case, the electromagnetic beam $E_{S1}$.

Furthermore, said articulated portion 480 comprises compressible means 486a, 486b, 488a, 488b allowing the flattening of the retaining system 400 against the inner faces of the housing provided for this purpose in the measurement module 100 when said articulated portion 480 is in the use position. Thus, the retaining system 400 is in permanent contact with the housing, in particular with inner faces of said housing. By being thus configured, the retaining system 400 of the device 1 has an identical mechanical and optical positioning from one use to the other without the user having to prove that they are authorised or to carry out a rigorous visual inspection. It therefore makes it possible to take repeatable measurements on varied samples. This configuration is therefore preferred to that where the retaining system is positioned at the level of the opening 150.

In any case, the sample has a fixed positioning within the measurement module 100.

In this regard, the sample S of which the properties are sought to be determined is solid. As already mentioned, this is more specifically a sample of grains, powders, doughs, and generally, products which are manufactured in the cereal or dairy industry. The sample can be of any size, the only limit being the dimensions of the reservoir 110. That being said, it is preferable that the size of the sample is adapted such that the quantity of sample sampled is representative of the assembly from which it has been extracted. The sample is heterogenous both in the size of its elements as in their shape. It can possibly contain impurities and generally, any foreign body which is not strictly speaking the preponderant element within the sample. Conventionally, the whole challenge of infrared spectroscopy and fluorescence spectroscopy measurements can moreover reside in the fact of determining the proportions of such foreign bodies so as to evaluate the quality of the sample S analysed. The sample can also be crushed beforehand, like for crisps or biscuits.

Returning to FIG. 1a, the first infrared spectroscopy subassembly 120 comprises a first excitation source 122, an optical element 140 and a first means 124 for acquiring transmittance spectra $S_{iR}$, $S_i$ of the sample S. As has been mentioned above, these elements are not all grouped together in a placement, distinct from the placement of the elements composing the second fluorescence spectroscopy subassembly, but arranged optimally with the latter.

The first excitation source 122 is configured to emit an electromagnetic radiation $E_{S1}$ in the infrared field. It can also emit in the near-infrared. It can, preferably, emit a polychromatic and wide spectrum electromagnetic radiation $E_{S1}$ in a range of wavelengths of between 700 and 1100 nm.

The first excitation source 122 emits electromagnetic radiation $E_{S1}$, in the form of a beam, to the first wall 112 of the reservoir. The electromagnetic beam $E_{S1}$ propagates along an optical axis X passing through the first excitation source 122 and centred on said first source 122. As the first wall 112 is transparent for the electromagnetic radiation $E_{S1}$, the latter is capable of passing through said first wall 112 and therefore of illuminating the inside of the reservoir 110 and the sample S, if necessary. Preferably, the first source 122 illuminates the wall 112 in a homogenous and collimated manner. By "collimated", this means the fact that the light from the first source has substantially parallel radiations, i.e. which are deployed without dispersing with distance.

As an example, an excitation source 122 suiting the implementation of the invention is a high-power and broadband halogen incandescence source. Further to its capacity to illuminate in the infrared field, this type of light source has a high inertia, which makes it possible to limit, even remove the scintillation effects due to fluctuations of the input current. In a variant to a wide spectrum source, several polychromatic or monochromatic sources could also be used covering the desired range of wavelengths.

The interactions between the infrared electromagnetic radiation $E_{S1}$ and the sample are of an elastic nature. They depend on the nature, on the force and on the axis of chemical bonds of molecules of the sample S analysed. The infrared electromagnetic radiation $E_{S1}$ is only absorbed if the scalar product of said electromagnetic radiation $E_{S1}$ with the electric dipolar moment induced during the vibration of the molecules is non-zero. Infrared spectroscopy therefore makes it possible to provide information about the structure and the chemical composition of the samples studied.

That being said, in order to be able to obtain quantitative information, it is used in infrared spectroscopy to take at least two measurements in order to measure the spectrum of the sample without impact of the other elements located on the optical path, which includes the source and the detector. It is also the case in the method for analysing a sample according to the invention. In this case, a general description is made of it in order to better understand the role of the optical element 140. A first transmittance spectrum $S_{iR}$, called reference spectrum, is acquired without sample, then a second transmittance spectrum $S_i$ is acquired with the sample. The reference spectrum $S_{iR}$ is the measurement of the contribution of the local environment in the spectrum $S_i$ obtained with the sample and must be compared with the spectrum $S_i$ obtained with the sample, in order to extract the real signal only due to the sample.

However, the intensity ratio between the reference spectrum $S_{iR}$ and the spectrum $S_i$ of the sample is very high, i.e. typically around 20000. Indeed, under identical illumination conditions in terms of intensity, the reference spectrum $S_{iR}$ has a very high transmittance, while the spectrum $S_i$ with the sample has a lower transmittance. In order to reduce this transmittance difference, two natural solutions have been proposed. The first consists of adding an absorbent element on the optical path between the source and the detection means during the measurement without sample. The absorbent element makes it possible to obtain intensities which are comparable with and without the sample, but alters the optical path between the two measurements. An additional "component" must therefore be considered in the spectra obtained and possibly removed, which can prove to be complex. The second solution consists of altering the spectrum of the source itself by making the light intensity vary between the two measurements. The problem which is thus posed is that of the repeatability of the measurements.

The optical element 140 of the analysis device 1 of the invention makes it possible to avoid such constraints. Indeed, the optical element 140 is diffusing and transparent for the infrared electromagnetic radiation $E_{S1}$ emitted by the excitation source 122. The transparency of the optical element 140 vis-à-vis the radiation $E_{S1}$ allows it to not impede the propagation of said radiation $E_{S1}$. The diffusing character of the optical element 140 itself makes it possible to deviate the electromagnetic radiation $E_{S1}$ in various directions and therefore makes it possible to reduce the intensity of the light signal arriving on the first acquisition means 124, in particular, in the absence of sample S in the reservoir 110. In this case, the diffusion phenomenon, is Rayleigh diffusion. The transparent and diffusing characters of the optical element 140 involve a certain number of phenomena which do not have the same scope, according to which the reservoir 110 comprises, or not, a sample.

Figure 2A:
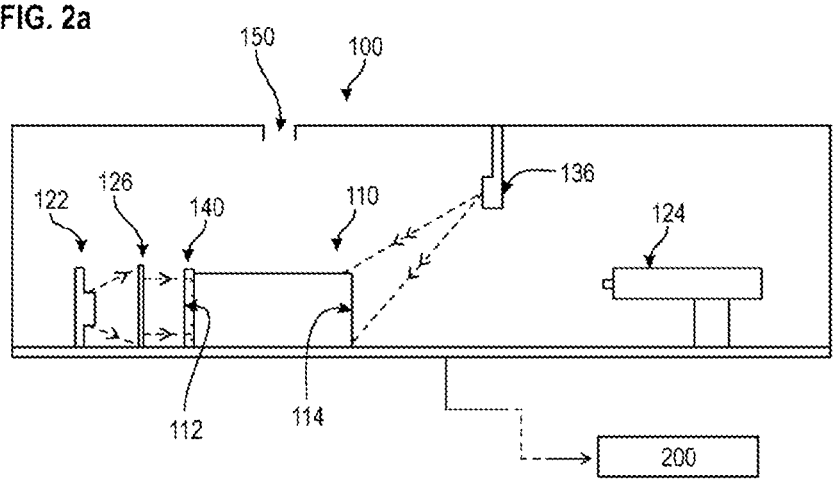
FIG. 2a is an illustration, as a side view, of the analysis device of FIG. 1a, FIG. 2b is an illustration, as a side view, of the analysis device of FIG. 1b.

According to a first embodiment illustrated in FIGS. 1a and 2a, the optical element 140 is positioned between the first excitation source 122 and the first wall 112 of the reservoir, on the optical path between the first source 122 and the first acquisition means 124. In other words, the optical element 140 is located both opposite the first excitation source 122 and the first wall 112 of the reservoir, without however being necessarily in the proximity of said first source 122 and said first wall 112 of the reservoir. In this embodiment of the invention, the optical element 140 constitutes more specifically the first wall 112 of the reservoir. In other words, the first wall 112 and the optical element 140 only form one. Also, in other words, the optical element 140 is integral with the reservoir 110. Thus, the optical element 140 being localised on the optical path of the electromagnetic radiation $E_{S1}$, it is positioned so as to interact with that before it reaches the first acquisition means 124.

In the absence of sample S in the reservoir 110, the beam $E_{S1}$ is brought to successively pass through the optical element 140/the first wall 112, then the second wall 114 of the reservoir before reaching the first acquisition means 124. By passing through the optical element 140, it can only propagate in multiple directions and reach the first acquisition means 124 with a reduced intensity without losing information. In the presence of the sample S in the reservoir 110, the beam $E_{S1}$ is brought to successively pass through the optical element 140/the first wall 112, then the sample S and finally the second wall 114 before reaching the second acquisition means 124. In consequence of which, even if the beam is made diffuse due to the optical element 140, this diffusion is negligible with respect to the diffusion naturally generated by the sample when this is passed through by the beam $E_{S1}$. The negligible character of the diffusion induced by the optical element 140 during the measurement with sample depends on the sample S analysed. If a sample S of grains or powder is naturally very diffusing and therefore more diffusing than the optical element 140, this is not necessarily the case for all the other types of sample. The signal measured with the sample S in the presence of the optical element 140 is therefore not of a lesser quality comparatively with the signal which would have been measured in the absence of the optical element 140. In short, the optical element 140 makes it possible to acquire the reference spectrum $S_{iR}$ and of the spectrum $S_i$ of the sample with the first excitation source 122 illuminating under the same conditions during the acquisition of the two spectra. This makes it possible to leave the choice of the acquisition means free.

The optical element 140 is not necessarily positioned parallel to the first wall 112, as is illustrated in the figures. Preferably, the optical element 140 generates an isotropic diffusion, in this case, in all directions. Thus, insofar as it is positioned on the optical path, it can be inclined with respect to the optical axis X without preventing the propagation of the infrared electromagnetic beam $E_{S1}$ about the optical axis X, while exercising its first function which is to make it diffuse. For example, the optical element 140 can be manufactured by frosting a glass.

Figure 1B:
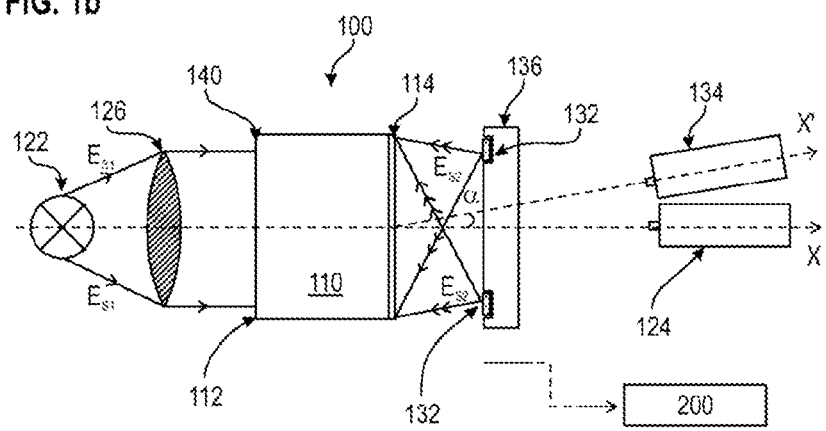
FIG. 1b is a schematic representation of an analysis device according to an embodiment of the invention, wherein the optical element is positioned between the first excitation source and the first wall of the reservoir, the optical element being a distinct element of the reservoir.
Figure 2B:
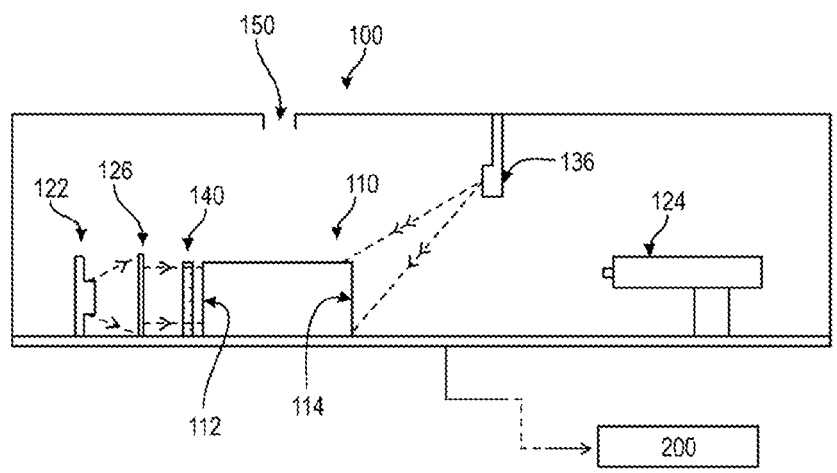

According to a second embodiment illustrated in FIGS. 1b and 2b, the optical element 140 and the first wall 112 of the reservoir can be separated. In this configuration, the optical element 140 is presented in the form of an element distinct from the first wall 112. It can possibly be located at a distance from the reservoir 110 and be stabilised by means of a support, but this is not compulsory. It can also be glued to the first wall 112 of the reservoir, without being said first wall 112. Whatever the configuration considered, i.e. that the optical element 140 constitutes the first wall 112 or is separated from it, which is important in the scope of the invention is that the optical element 140 is localised on the optical path of the electromagnetic beam $E_{S1}$ before this reaches the first acquisition means 124.

The first subassembly 120 can comprise, further to the optical element 140, a collimation lens 126 for the excitation source 122 located on the optical path of the electromagnetic beam $E_{S1}$. Preferably, the collimation lens 126 is located between the excitation source 122 and the optical element 140, that the latter is integral with the reservoir 110 or separated from it. The collimation lens 126 makes it possible to make the electromagnetic beam $E_{S1}$ coming from the excitation source 122 parallel, such that the inside of the reservoir 110, in particular the sample S, is illuminated homogenously. The information obtained from the measurement are all the more qualitative and quantitative.

In a variant of the embodiment of the first and second embodiments of the invention, the optical element 140 could both make it possible to make the electromagnetic beam $E_{S1}$ diffuse and at the same time, collimate it. In this case, the collimation lens 126 is not necessary, since the optical element 140 plays the role of said collimation lens by fulfilling its first function which is to make the radiations coming from the first excitation source 122 diffuse. For example, such an element can be manufactured by frosting a collimation lens.

Furthermore, as mentioned above, the first subassembly 120 comprises a first means 124 for acquiring transmittance spectra. In this regard, the first acquisition means 124 makes it possible to detect an electromagnetic signal emitted in the visible, near-infrared and infrared fields, in particular at wavelengths of between 750 and 2500 nm. As has been seen in the sections above, the use of the optical element 140 leaves the choice of the acquisition means free.

In a preferred embodiment of the invention, for this first acquisition means 124, one single charged transfer detector or charged coupled device (CCD) sensor. It is also possible to use a complementary metal oxide semiconductor (CMOS) sensor-based detector, with the basis of photodiodes or any other detection means known to a person skilled in the art. In practice, it is preferable to use the detector with a monochromator. The monochromator makes it possible to select the desired spectral field(s), i.e. adapting the collection of the signal to the analysis considered. Considerable monochromators are, for example, one (or more) chromatic filter(s) or also a spectrograph.

The first acquisition means 124 is advantageously aligned with the excitation source 122, the diffusing and transparent optical element 140 and the reservoir 110 along the optical axis X. In other words, these elements are all on the optical path. The first acquisition means 124 has a field angle centred around the optical axis X. For all that, what is important in this case is that the first acquisition means 124 is arranged so as to detect the reference signal(s) $S_{iR}$ and the signal(s) $S_t$ with the sample emitted under illumination of the infrared beam $E_{S1}$.

If, from the standpoint of the infrared spectroscopy subassembly 120, the arrangements such as described above making it possible to take infrared spectroscopy measurements are ingenious in that they provide the diffusing and transparent optical element 140, they are even more so, in that they do not impede the fluorescence spectroscopy measurements taken on the same sample S. This is more specifically described below.

The second fluorescence spectroscopy subassembly 130 comprises a second excitation source 132 and a second means 134 for acquiring fluorescence signals $S_{f1}$, $S_{f2}$ of said sample S.

The second excitation source 132 is configured to emit an electromagnetic radiation $E_{S2}$ in the ultraviolet field. It can further emit in the visible field. According to a preferable embodiment, it can emit a monochromatic radiation having a wavelength of between 250 and 550 nm. An example of a second excitation source 132 which could be used in the analysis device 1 according to the invention consists of at least one light-emitting diode (LED) emitting a wavelength of 280 nm, 340 nm, 385 nm or 420 nm. The advantage of LED sources is their capacity to intensely and homogenously illuminate. Furthermore, they have a long service life.

Figure 3:
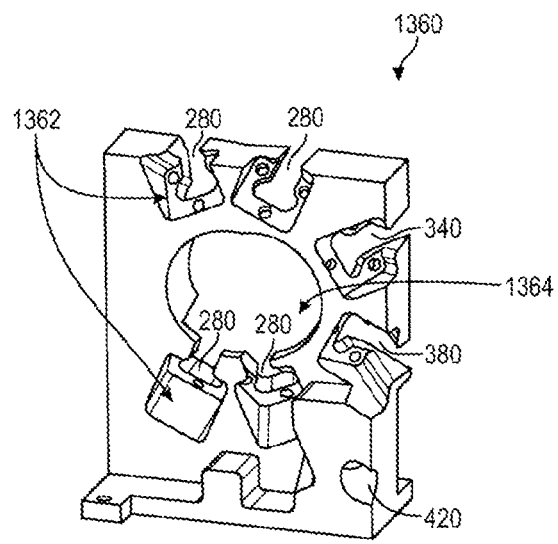
FIG. 3 is an illustration, in perspective, of a support for the second excitation source.

Preferably, the number of excitation sources 132 can be adapted according to the size of the surface to be analysed. When several second excitation sources 132 are used, a support 136 can thus be provided, as represented in FIGS. 1a and 1b, configured to accommodate the sources 132 and thus hold the sources on one single support. In this regard, in an example of an embodiment illustrated in FIG. 3, the support 136 comprises an assembly portion 1360 and a support portion (not illustrated) making it possible to stabilise the assembly portion 1360. The assembly portion 1360 comprises a plurality of housings 1362 disposed in a circle around a central opening 1364 of the support, and wherein the second sources 132 are capable of being fixed. Indeed, the housings 1362 have suitable dimensions for receiving the second sources 132 and comprise means for fixing the sources 132 making it possible to hold sources for example by means of screws and/or nuts. Preferably, the assembly portion 1360 is removable so as to be able to be removed from the support 136.

In a variant, a wide spectrum source could also be used as a second excitation source 132, emitting an electromagnetic radiation $E_{S2}$ in the ultraviolet field and a monochromator combined with such a source. In this configuration, the wide spectrum source being of polychromatic nature, it is necessary to associate it with a monochromator in order to select a narrower range of wavelengths or a wavelength from the electromagnetic beam $E_{S2}$ of a wider spectrum. This configuration is more complex than the preceding one, i.e. with the LED sources. An example of a wide spectrum source emitting in the ultraviolet field is a deuterium lamp which emits in an ultraviolet field at wavelengths of between 180 nm and 370 nm.

The second excitation source 132 emits the electromagnetic beam $E_{S2}$ to the second wall 114 of the reservoir, on the opposite side of the reservoir 110 where the diffusing and transparent optical element 140 is localised according to the first and second embodiments (FIGS. 1a, 1b, 2a, 2b). The second excitation source 132 can be off-centre with respect to the optical axis X. When several sources 132 are used, each of the sources can be off-centre with respect to said optical axis X, as is illustrated in FIGS. 4a to 4c. The source(s) 132 is/are advantageously inclined in the direction of the centre of the second wall 114, which allows a homogenous and suitable illumination of said second wall 114 by said sources. What is important in the present case, is that the second sources 132 are positioned so as to not prevent the acquisition of infrared and fluorescence spectra.

The fact that the second source 132 emits the electromagnetic beam $E_{S2}$ to the second wall 114 is neither anecdotic nor a simple choice of arrangement. As has been mentioned before the detailed description of the invention, it is a question in the present invention of providing a device 1 making it possible to take infrared spectroscopy and fluorescence spectroscopy measurements in reduced time on the same sample S without having to take the measurements in separate submodules, and therefore without having to separate the sample in two or also having to transport it from one module to another. This choice of arrangement makes it possible to take infrared spectroscopy and fluorescence spectroscopy measurements on the same sample, without the elements of the first subassembly 120, necessary for the infrared spectroscopy measurements, disrupting the fluorescence spectroscopy measurements.

Indeed, the very low intensity of the fluorescence regarding the intensity of the source makes it very sensitive to diffusion phenomena, the diffusion itself being dependent on the physicochemical nature of the sample. A diffusion, even of low intensity, disrupts, i.e. interferes with the fluorescence signal. If it does not prevent extracting quantitative data from it, the component due to the diffusion of the spectra significantly complexifies the extraction of useful data for the analysis and/or requires the use of filters which, currently, have a very limited effect on the reduction of the share of light due to the diffusion in the final spectrum.

Due to its positioning between the first excitation source 122 and the first wall 112 of the reservoir, the diffusing optical element 140 can play its role for the infrared spectroscopy measurements without impeding the fluorescence spectroscopy measurements. Indeed, the fluorescence spectroscopy measurements only require an illumination of the reservoir 110, if necessary of the sample S on the side of the second wall 114, i.e. on the side opposite the diffusing optical element 140. No interaction can therefore occur between the electromagnetic beam $E_{S2}$ emitted by the second excitation source 132 and the optical element 140. The ingenious arrangement of the elements of the module 100 and the optimised illumination directions of the reservoir 110 and of the sample S with the first 122 and second 132 excitation sources make it possible to take two types of measurements without one "interfering with" the other. Thus, the challenge of the invention which is to be able to take infrared spectroscopy measurements and, within a reduced timeframe of being able to take fluorescence spectroscopy measurements on the same sample, is reached. This arrangement also makes it possible that the second subassembly 130, necessary for the fluorescence spectroscopy measurements, does not disrupt the infrared spectroscopy measurements.

It must be noted that if the diffusing optical element 140 is located between the first excitation source 122 and the first wall 112 of the reservoir in the first and second embodiments of the invention, another positioning can be considered by a person skilled in the art, while remaining in the inventive concept of the invention, as long as said optical element 140 is positioned so as to not impede the fluorescence spectroscopy measurement and that it is positioned between the first excitation source 122 and the first acquisition means 124. The optical element 140 is positioned so as to not impede the fluorescence spectroscopy measurements as long as it does not disrupt the electromagnetic beam $E_{S2}$ emitted by the second acquisition means 134 and that it does not disrupt the fluorescence signal emitted by the sample when it is exposed to such a beam. The optical element 140 is positioned between the first source 122 and the first acquisition means 124 as long as it is positioned so as to make the radiation $E_{S1}$ emitted by said first source 122 diffuse without preventing its detection by the first acquisition means 124 during measurements with and without sample, by considering the abovementioned constraints.

Figure 1C:
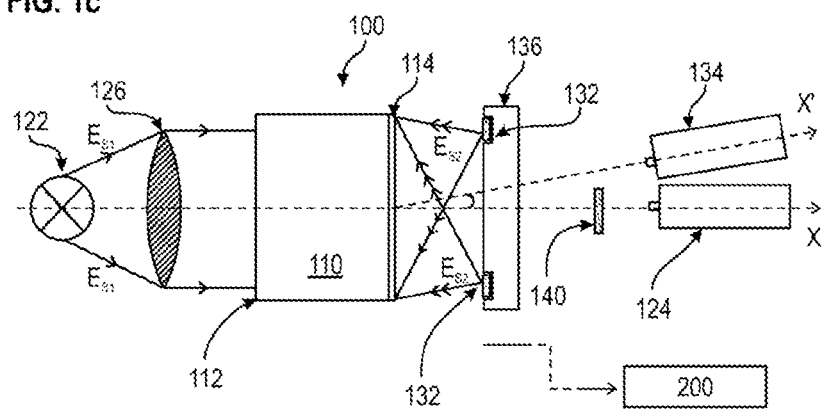
FIG. 1c is a schematic representation of an analysis device according to an embodiment of the invention, wherein the optical element is located between a second wall of the reservoir and a first excitation source.

Thus, in another embodiment of the invention, the optical element 140 can also be positioned between the second wall of the reservoir 114 and the first acquisition means 124, outside of an optical path of the electromagnetic radiation $E_{S2}$ emitted by the second excitation source 132 and outside of a solid angle for collecting a fluorescence signal emitted by the sample S when electromagnetic radiation $E_{S2}$ emitted by the second excitation source 132 is exposed. In this embodiment, the second wall 114 of the reservoir cannot be constituted of the optical element 140 since this would necessarily impede the fluorescence spectroscopy measurement. An example of a device 100 corresponding to such an implementation is illustrated in FIG. 1c.

Furthermore, the second wall 114 of the reservoir is transparent for the electromagnetic radiation $E_{S2}$ emitted by the second source 132, such that said radiation $E_{S2}$ is capable of passing through the second wall 114 and therefore of illuminating the inside of the reservoir 110 and the sample S. Furthermore, the second wall 114 of the reservoir is anti-reflective for the electromagnetic radiation $E_{S2}$. The anti-reflective character of the second wall 114 makes it possible to increase the share of light which is transmitted through the second wall 114 and which reaches the sample S. This therefore makes it possible to improve the detection of the fluorescence signal which can prove to be relatively low and therefore makes it possible to optimise the fluorescence spectroscopy measurements.

Furthermore, the second wall 114 of the reservoir is also transparent for the infrared electromagnetic radiation $E_{S1}$ emitted by the first excitation source 122 and for the infrared electromagnetic radiation reemitted by the sample S or the environment neighbouring it.

In this regard, as has been mentioned above, the support 136 also comprises a central opening 1364. The opening 1364 is central in that it leaves a wide empty zone with no material around the optical axis X, which makes it possible to let the electromagnetic radiation generated by the infrared spectroscopy and fluorescence spectroscopy measurements pass through. The opening 1364 is of a size suitable for letting as many beams as possible pass through, which makes it possible to collect a maximum amount of signals for the infrared spectroscopy measurement. In the example of an embodiment illustrated, the central opening 1364 is circular-shaped, but this is not compulsory. The central opening 1364 can adopt any other shape as long as it does not impede the collection of the infrared signal.

The second acquisition means 134 is dedicated to the fluorescence spectroscopy measurement. In this regard, the second acquisition means 134 makes it possible to detect the electromagnetic signal emitted in the ultraviolet and visible fields, and more specifically at wavelengths of between 200 and 550 nm. The second acquisition means 134 can be a CCD sensor, a CMOS sensor, a photodiode or any other detection means known by a person skilled in the art. It is preferable to use the detector with a monochromator, for example one (or more) chromatic filter(s) or also a spectrograph.

The second acquisition means 134 advantageously makes an angle α with the optical axis X. In other words, an axis X' passing said second acquisition means 134 and a median plane and substantially orthogonal to the second wall 114 of the reservoir makes an angle α with the optical axis X. The axis X' is therefore the axis that has the second acquisition means 134 with respect to the optical axis X. Thus, the second means 134 is not optically aligned with the other elements of the module 100, namely the first excitation source 122, the optical element 140, the reservoir 110, the second excitation source 132 and the first acquisition means 124. It results from this that the second source 132 emits an electromagnetic radiation $E_{S2}$ on either side of the optical axis X, only the portion of this electromagnetic radiation localised in a field angle of the second acquisition means 134 around the direction of axis X' is detectable.

The illumination of the second wall 114 by the second source 132 generates the specular reflection which remains significant, despite an anti-reflective processing of the second wall 114 of the reservoir. The reflection is called specular, when the incident radiation is reflected in a given direction in the manner of a beam reflected by a mirror. It can cause the saturation of the detection means, since there is still a significant share of electromagnetic radiation which is reflected in a specular manner in the direction of the optical axis X. In this case, the second excitation source 132 emits the electromagnetic radiation $E_{S2}$ to the second wall 114, which is passed through by said optical axis X, which necessarily generates the specular reflection. The angle α that makes the second acquisition means 134 with the optical axis X is chosen such that said second acquisition means 134 is not directly positioned on the optical path of the beams reflected in a specular manner by the second wall 114 of the reservoir, which makes it possible to avoid the saturation of said second acquisition means 134, while keeping the maximum amount of fluorescence emitted in an isotropic manner by the sample. For example, the angle α takes a value equal to 10°.

The measurement module 100 such as described above makes it possible to group in one single module, the elements making it possible to take both infrared spectroscopy and fluorescence spectroscopy measurements without having to separate the sample in two portions, and therefore to have to make two separate analyses spatially, even can be temporally, or also without having to take two types of measurement successively over time. If the device 1 according to the invention makes it possible to take the measurements by the two types of spectroscopy on the same sample S within a timeframe of a few minutes, it is also configured to process the data which result from this.

In this regard, the device 1 according to the invention comprises, in addition to the measurement module 100, a processing module 200 connected to the measurement module 100. The processing module 200 can be of any type of electronic or computerised processing means, for example, a computer, a smartphone or any similar appliance at a terminal with a control screen, a USB stick, a mobile memory card or any other similar technology. Preferably, the processing module 200 is an embedded PC.

The processing module 200 is connected to the single measurement module 100 of the analysis device 1 by means of a communication network 300. The communication network 300 makes it possible to connect the processing module 200 to the measurement module 100. For example, the communication network 300 is a local network such as a wired network, a Bluetooth network, a Wi-Fi network or also an Ethernet network. In any case, the communication network 300 is configured to transmit information between the processing module 200 and the measurement module 100 of the device 1. Because the measurement module 100 is unique, there is therefore no interface between the measurement and the processing.

The processing module 200 comprises a processor 220 and a memory 240.

The memory 240 is configured to receive and store the data transmitted by the communication network 300. These data can comprise any type of information measured by the measurement module 100 such as wavelengths of infrared $E_{S1}$ and fluorescence Est radiations emitted by the sample, intensities measured from these radiations or also corresponding electromagnetic spectra.

The processor 220 is configured to analyse and/or process the data obtained by infrared spectroscopy and fluorescence spectroscopy. In this regard, software for processing these data can be installed on the processor in order to automate the processing of these data in real time. What is important in the scope of the present invention is that the processor 220 is able to process the data coming from the infrared spectroscopy measurements and those coming from the fluorescence spectroscopy measurements sequentially and within a timeframe of a few minutes to extract assessment factors and/or criteria of it from the sample S studied. The operations performed by the processor 220 will be described in more detail below relative to the method for analysing a sample S.

Indeed, the invention further relates to a method for analysing a sample S implemented by means of an analysis device 1 such as described above. The method according to the invention comprises the following steps.

During a first step A), a transmittance spectrum $S_i$ is acquired from the sample S by means of said first infrared spectroscopy subassembly 120. If in theory, it is possible to take such a measurement directly, it is not possible to quantify with precision the phenomenon specific to the sample, i.e. transmittance of the sample, without an additional measurement of the reference infrared spectrum $S_{iR}$ otherwise called spectrum without sample. As has been described above, the measurement of the reference spectrum $S_{iR}$ makes it possible to quantify the contribution of the local environment in the measurement of the transmittance spectrum of the sample.

Step A) of the method according to the invention advantageously comprises substeps Aa), Ab), Ac), Ad) and Ae), steps Aa) and Ab) relating to the measurement of the reference spectrum $S_{iR}$ and are therefore carried out with the sample to be analysed while steps Ac) to Ae) relate to the measurement of the spectrum $S_i$ of the sample and therefore are implemented with the sample to be analysed.

During substep Aa), the reservoir 110 is illuminated by means of an electromagnetic radiation $E_{S1}$ generated by the first source 122. The electromagnetic beam $E_{S1}$ passes through the optical element 140, then the first wall 112, inside the reservoir and the second wall 114 of the reservoir, in this order, before reaching the first acquisition means 124. The electromagnetic beam $E_{S1}$ thus describes a path along the optical axis X. The inside of the reservoir being empty, it does not comprise any sample. Furthermore, the reservoir 110 remains filled with air and other elements present in the air, which can absorb and reflect some of the electromagnetic radiation $E_{S1}$.

It is specified that if the first wall 112 of the reservoir is constituted by the optical element 140, the beam $E_{S1}$ will therefore successively pass through the optical element 140, the inside of the reservoir and the second wall 114 of the reservoir before reaching the first acquisition means 124. It is also specified that, if a collimation lens 126 is optionally interposed between the first excitation source 122 and the optical element 140, the order of passage through the different elements will be impacted together. Also, it is specified that in an embodiment where the second excitation source 132 comprises a plurality of sources supported by the support 136, the electromagnetic beam $E_{S1}$ necessarily passes through the opening 1364 of said support which is positioned on the optical path.

During substep Ab), the reference transmittance spectrum $S_{iR}$ is measured.

During substep Ac), the reservoir 110 of the sample S to be studied is filled. If comparative measurements must be taken between several samples, the reservoir 110 will be systematically filled with the same quantity of sample.

During substeps Ad) and Ae), steps Aa) and Ab) are repeated, with the difference that in this case, the sample S to be studied is placed inside the reservoir 110. At the end of this second acquisition sequence, the transmittance spectrum $S_i$ of the sample is obtained.

The data collected during step A), in particular the reference transmittance spectra $S_{iR}$ and $S_i$ of the sample are then analysed and/or processed by the processor 220. Preferably, they are stored in the memory 240 of the processing module. This will be returned to below.

During a step B of the method according to the invention, fluorescence spectra $S_{f1}$, $S_{f2}$ of said sample S are acquired by means of the second fluorescence spectroscopy subassembly 130. The sample S which this relates to is strictly the same sample analysed during step A). In other words, this is not a sample which would have been divided to take the two types of measurement. Moreover, it must be specified that step B) is not necessarily implemented after step A). It can equally be carried out before or after step A).

Step B) of the method comprises substeps Ba), Bb), Bc) and Bd) which are described below. With a constant integration time, when the fluorescence spectroscopy measurement is taken on an extended range of wavelengths, for example of between 250 nm and 650 nm, the intensity of the signal can be utilisable over a portion of this range of wavelengths, while it cannot be utilisable over another portion of this range of wavelengths and saturate the acquisition means. This comes from the dynamic range between diffusion and fluorescence. Indeed, a fluorescence spectrum always comprises a range of wavelengths on which the diffusion and a range of wavelengths is measured, on which the fluorescence signal per se is measured. However, the maximum intensity of the signal measured coming from the diffusion is greater than that coming from the fluorescence phenomenon. The intensity ratio measured between the two measurements can be around equal to 100. Yet, these two components of the signal are of equal importance for the purpose of the physicochemical analysis of the sample. It is therefore desirable to return them to comparable intensity levels.

During a first substep Ba), the reservoir 110 and the sample S are illuminated by means of the electromagnetic radiation $E_{S2}$ emitted by the second excitation source 132. Given the arrangement of the elements of the second subassembly 130, the electromagnetic beam $E_{S2}$ emitted by the first source 132 passes through the second wall 114 of the reservoir then the sample in this order. The interaction of the electromagnetic beam $E_{S2}$ with the sample S thus generates a fluorescence signal specific to said sample S.

During a second substep Bb), a first fluorescence spectrum $S_{f1}$ of said sample S is acquired simultaneously with step Ba) by means of the second acquisition means 134 with a predetermined integration time $t_1$. The determination of this integration time can require prior measurements according to the sample S to be studied in order to optimise either the signal share due to diffusion, or the signal share due to fluorescence. The signal is considered as optimised when the signal/noise ratio is sufficiently high to allow the extraction of the desired parameters. Whatever it is, and as is mentioned in the sections above, the signal measured by the second acquisition means 134 can, given the contribution of these two phenomena, i.e. diffusion and fluorescence, in the final spectrum prove to be unusable over a portion of this range of wavelengths.

During a third substep Bc) and a fourth substep Bd), substeps Ba) and Bb) are repeated, but this time, by selecting an optimised integration time $t_2$ to measure the other component of the signal, i.e. either the signal share due to diffusion, or the signal share due to fluorescence for which the integration time had not been optimised during substep Bb). Coming from these steps, a second fluorescence spectrum $S_{f2}$ is obtained.

It is considered, for example, that it is sought to measure the fluorescence signal over a range of wavelengths of between $\lambda_1$ and $\lambda_n$. With the integration time $t_1$, the fluorescence signal was unusable over a range $\lambda_1$ to $\lambda_m$ although being utilisable over the rest of the range, i.e. $\lambda_{m+1}$ to $\lambda_n$, i being the step between the measurements. During the acquisition sequence of $S_{f2}$, an integration time $t_2$ greater than $t_1$ will be chosen, if the pattern for which the fluorescence signal was unusable over the range $\lambda_1$ to $\lambda_m$ is a low signal/noise ratio or, on the contrary, an integration time $t_2$ less than $t_1$ will be chosen, if the pattern for which the fluorescence signal was unusable over the range $\lambda_1$ to $\lambda_m$ is a saturation of the second acquisition means 134.

Thus, at the end of the second step B) of the method according to the invention, two fluorescence spectra $S_{f1}$ and $S_{f2}$ are obtained, which are collected then processed by the processor 220. It is also reminded that the reference infrared spectrum $S_{iR}$ and the infrared spectrum $S_i$ of the sample associated with the infrared spectroscopy measurement are also collected and processed by the processor 220.

Although in the embodiment described above, step B) of fluorescence spectroscopy measurements is carried out after step A) of infrared spectroscopy measurements, it is also possible to carry out step B) before step A) without any prejudice, since the steps are independent.

During a third step C) of the method according to the invention, the data obtained by infrared spectroscopy and fluorescence spectroscopy are analysed, by means of the processing module 200, the processor 220 being configured to determine at least one indicator characterising said sample from data coming from the analysis. Step C) of the method according to the invention is a step implemented by computer. The word "computer" has a broad meaning and means any means equipped with a processor and capable of executing tasks according to commands which have been programmed. Whatever it is, coming from step C), at least one indicator characterising the sample S studied is obtained. In this regard, it can, without doubt, be specified that this step is preferably implemented after steps A) and B).

Below, in turn, the processing of infrared and fluorescence spectra obtained from steps A) and B) respectively will be mentioned.

During a first substep Ca), a final transmittance spectrum $S_{if}$ of the sample S is determined from the reference spectra $S_{iR}$ and $S_i$ of the sample. In this regard, a median smoothing at more or less one (±1) pixel can be first applied to remove the faulty pixels in the reference infrared spectra $S_{iR}$ and $S_i$ of the sample. Then, second, this is removing the contribution of the environment local to the spectrum $S_i$ of the sample. For this, the ratio between the signal $S_i$ of the sample and the reference signal $S_{iR}$ is calculated. At this stage, it must be noted that the intensity ratio between the two spectra is typically 1000. The use of the diffusing optical element therefore makes it possible to divide by 20, the intensity ratio between the measurement without sample $S_{iR}$ and the measurement with sample $S_i$. Thus, the final transmittance spectrum $S_{if}$ is obtained. A standardisation of the spectrum thus obtained can also be performed to return it to the percentage values.

During a second substep Cb), a final fluorescence spectroscopy spectrum of the sample S is developed from the spectra $S_{f1}$ and $S_{f2}$ (considering the example mentioned above). This spectrum is called "final spectrum" $S_{ff}$ below. A concatenation of the spectra is carried out in 1) recovering the optimised spectrum from the diffusion signal in the spectrum $S_{f1}$ or $S_{f2}$ measured for this purpose, 2) recovering the optimised spectrum from the fluorescence signal in the other spectrum $S_{f1}$ or $S_{f2}$ measured for this purpose, and 3) by grouping together the optimised diffusion and fluorescence spectra in order to obtain a final spectrum $S_{ff}$ having a good signal/noise ratio as much for the spectral components due to diffusion as for the spectral components due to fluorescence. The signal/noise ratios of the spectrum share due to diffusion and the spectrum share due to fluorescence are thus returned to a value of 100 over the whole spectrum, in particular over the portion of the spectrum corresponding to the fluorescence component, which is greater than the ratio of 10 in the absence of processing. The ranges of wavelengths on which the spectra $S_{f1}$ and $S_{f2}$ extend are specified below.

By continuing with the preceding example, the spectrum $S_{f1}$ corresponding to an optimal measurement of fluorescence performed over a range of wavelengths of between $\lambda_{m+i}$ to $\lambda_n$ can thus be concatenated—i is a natural integer corresponding to the step—with the spectrum $S_{f2}$ corresponding to an optimal measurement of diffusion performed over a range of wavelengths of between $\lambda_1$ to $\lambda_m$. The final fluorescence spectrum $S_{ff}$ thus obtained extends between $\lambda_1$ to $\lambda_n$ and has a good quality, as well in the portion of the spectrum associated with the signal share coming from diffusion, as that associated with the signal share coming from fluorescence. The concatenation can also make it possible to concatenate spectra which have only been able to be measured with different sources 132, for example because of cut-off wavelengths defined by the LEDs. A last substep would consist of performing a Gaussian smoothing of the final spectrum $S_{ff}$ thus obtained.

In practice, one from among the spectra $S_{f1}$ and $S_{f2}$ corresponds to the "diffusion" component of the fluorescence spectrum and extends over a range of wavelengths substantially of between 250 nm and a concatenation wavelength while the other from among the spectra $S_{f1}$ and $S_{f2}$ corresponds to the "fluorescence" component of the fluorescence spectrum and extends over a range of wavelengths substantially of between the concatenation wavelength of 650 nm, even more than 650 nm. The concatenation wavelength is located beyond the excitation wavelength (i.e. the electromagnetic radiation $E_{S2}$ wavelength) is at the minimum value in a range of wavelengths close to the excitation wavelength. In the case of the measurement of cereal grains, the concatenation wavelength is equal to the excitation wavelength to which is added between 10 and 20 nm.

Thanks to this coupled measurement system, the acquisition of a fluorescence emission infrared transmittance spectrum on the same subsample makes it possible to group all of the spectral information provided by these two optical technologies, partially complementary information, to enrich the knowledge of the heterogenous sample analysed. Thanks to the device implemented, the coherence between the information acquired by the two infrared and fluorescence technologies, since the spectra correspond to the same sample, ideally makes it possible, and for the first time, to collect them to perform a merging of the information contained in each of the spectra.

It is highlighted that in the method of the prior art, called reference method, the third and fourth substeps Bc) and Bd) do not exist. Only the fluorescence spectrum $S_{f1}$ is acquired with unique operating parameters. The consequence being that either the component of the signal due to diffusion is optimised, or the component of the signal due to fluorescence is optimised, or none of the two is optimised. Thus, according to the reference method, the final fluorescence spectrum $S_f$ corresponds to the spectrum $S_{f1}$ since no spectrum $S_{f2}$ is acquired.

In addition, from the method for concatenating spectra seen above, other methods can be implemented to utilise the information from these fluorescence and infrared spectra, several methods are possible.

But, before anything else, the infrared and fluorescence emission transmittance spectra must, initially, be processed then merged. This is pre-processing.

The fluorescence spectra are processed to isolate the diffusion of the fluorescence spectrum and thus obtain a pure fluorescence spectrum. To do this, several methods can be considered:

Truncation of the diffusion spectrum if this (diffusion) does not overlap with the fluorescence spectrum Modelling of the form of the diffusion and removal of the modelled diffusion Use of chemometric tools like ICA (Independent Component Analysis) which make it possible to differentiate the diffusion signal and the pure fluorescence signal.

From that, for each measurement, as many fluorescence emission spectra as excitation (LED) wavelengths are achieved, and an infrared transmittance spectrum.

There are two main approaches for coupling the signals. They differ by the order in which they will, on the one hand, couple the information, and on the other hand, reduce this information from a number of variable of a few thousand, to one or two tens, without loss of useful information. Different calibration or classification models can be applied to these new variables in a reduced number.

The two main approaches are therefore as follows:

A low-level approach, which couples the reduced information, or scores, coming from the breakdown of each spectrum. Below, the possible variable reduction methods are shown. Thus, a restricted number of variables is obtained, which contains almost all the initial information. These variables can thus be modelled by different calibration or classification algorithms.

A high-level approach, which consists of coupling the spectra themselves before proceeding with the variable reduction step. The best way of coupling the spectral information is to concatenate the spectra. Then, various variable reduction techniques, like, in this case also, analysing principal components, can be applied. The reduced information combining the two technologies will thus be introduced in the calibration models, like multilinear regression, or classification.

Now, the various techniques which could be applied for each of these operations will be explored.

Concatenation: the spectra are organised end-to-end, preferably, each fluorescence emission spectrum according to the increasing excitation wavelengths, then the infrared transmittance spectrum. Several precautions will, in this case, be taken:

Such that each spectrum has the same weight within the assembly, the spectra must be standardised and thus give them a similar intensity. For example, a standardisation can be performed by the area, a standardisation by standard deviation of the spectrum followed by a centring, or also a standardisation by the maximum such that intensities vary between 0 and 1.

Then, it must be ensured not to generate any rupture between the signal of the last wavelength of the spectrum N-1 and the signal of the first wavelength of the following spectrum N. To do this, various techniques are possible, like forcing the value to zero if the portion of the spectrum in question does not contain information. It all must, despite everything, smoothen the spectrum to obtain a regular signal.

This is the method seen above.

Reduction of information: this reduction of information from spectral variables is also called spectrum breakdown. Each intensity at each measured wavelength corresponds to a variable, then there is a very high redundancy between all of these variables (highly correlated variables). The idea is therefore to extract the independent information, the sum of which covers all of the initial information contained in the spectrum.

The most known breakdown method is the analysis of principal components which ensures that each new variable, called principal component, constitutes a vector orthogonal to the system composed of other principal components. The number of components is determined by the capacity of the model to explain all of the spectral variance. However, from a certain level of breakdown, this variance now contains only noise.

In the case of multipath structures, like the 3D fluorescence structure, multipath techniques can be applied, such as PARAFEC (PARAllel FACtor analysis). This is about identifying single 3D structures, or factors, or also single fluorophores, which grouped together, contain all of the fluorescence acquired.

Calibration

Whatever the spectrum breakdown technique, single or concatenated, new variables are obtained, called single factors or principal components, in a limited number, of around 10 to 20 generally. Each sample is thus represented by a linear combination of these variables and by specific weights for each of them. These weights generally have the name of the scores.

$$Echi = a_{i1} \times V_1 + a_{i2} \times V_2 + \ldots a_{in} \times V_n + \text{Constant}$$

Where $a_{in}$ is the weight of each variable $V_n$ and n the number of variables obtained during the breakdown.

The scores therefore characterise the sample i for this breakdown.

During the calibration, therefore only these scores are used that the responses of interest are connected, that it is sought to predict by the spectral measurement.

The most common calibration methods are PCR (Principal Component Regression), or also MLR (Multiple Linear Regression) for linear mode calibrations.

There is another linear regression method, PLS (Partial Least Square) which has as a particularity and advantage of reducing the concatenated spectra in new variables, while considering correlations with the response to be calibrated and to be predicted. Reduction and calibration are done therefore in one single step.

Also, non-linear methods can be used as random forests or close neighbour techniques, or also neurone networks.

Example of an Embodiment of the Analysis Device 1 According to the Invention Whatever the example considered below, the processing module 200 is a computer, but it could be any device equipped with a processor 220, such as has been defined in the sections above. As regards the communication network 300, it is wired. That being said, it could be of any other nature.

Below, the elements of the measurement module 100 which have been described in the detailed description are interesting.

In an example of an embodiment of the analysis device 1, the optical element 140 consists of a glass wall distributed by Edmund Optics under reference 84479 and equipped with a diffuser, also distributed by Edmund Optics under reference 83420. The diffuser consists of a high-quality frosted glass which has a sufficient roughness to create diffusion. The glass can be frosted by using a sanding method which makes it possible to obtain a uniform diffusion over the whole surface.

In an example of an embodiment of the analysis device 1, the first excitation source 122 consists of a high-power and broadband halogen incandescence lamp distributed by Newport under reference 6335. It emits an electromagnetic radiation in the infrared, between 750 nm and 2500 nm.

In an example of an embodiment of the analysis device 1, the collimation lens 126 is distributed by Newport under reference KBX139.

In an example of an embodiment of the analysis device 1, the second excitation source 132 consists of a plurality of LEDs. There are seven LEDs of the first LEDs, four in total, which emit an electromagnetic radiation at a wavelength of 275 nm and are distributed under reference CUD7GF1B by HTDS. A second LED emits an electromagnetic radiation at a wavelength of 338 nm and is distributed under reference CUD4AF1B by HTDS. A third LED emits an electromagnetic radiation at a wavelength of 285 nm and is sold by HTDS under reference CUN8AF1B. A fourth LED emits an electromagnetic radiation at a wavelength of 420 nm and is sold by Roithner under reference LED420-01. All of the LEDs can be secured on a factory-made support 136.

In an example of an embodiment of the analysis device 1, a collimation lens can also be used combined with the second source 132. Such a collimation lens is distributed by Edmund Optics under reference 49556.

In an example of an embodiment of the analysis device 1, the first acquisition means 124 consists of an avaspec-2048XL spectrometer distributed by Optoprim.

In an example of an embodiment of the analysis device 1, the second acquisition means 134 consists of an avaspecULS-2048L spectrometer distributed by Optoprim.

In an example of an embodiment of the analysis device 1, the reservoir 110 comprises a sample detector window referenced WW10530-B by Thorlabs. The reservoir 110 can also comprise a presence detector referenced VCNL4040M3OE by Mouser. Such an item of equipment makes it possible to improve the automation of the analysis method according to the invention.

In an example of an embodiment of the analysis device 1, the reservoir 110 can be equipped with a temperature sensor. The temperature sensor can consist of a window capturing the temperature distributed by Thorlabs under reference WW70530. Another suitable temperature sensor is sold by Mouser under reference MLX90614ESF-ACC-000-SP. Knowledge of the temperature can be very useful for controlling the development of the sample.

Example of a Practical Implementation of the Method of the Present Invention

Figure 6A:
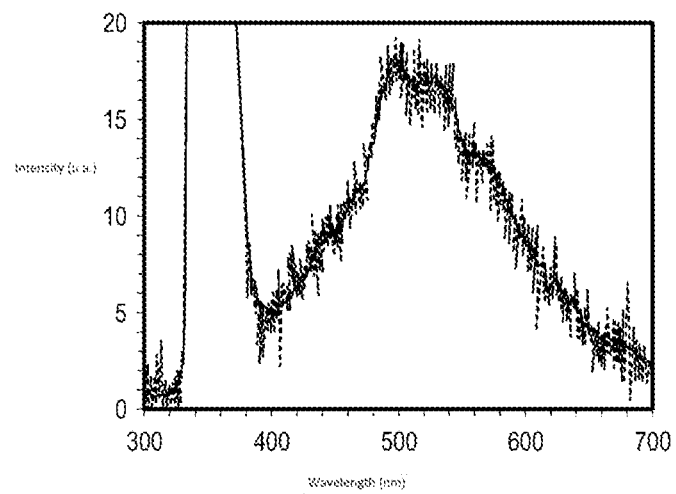
FIG. 6a illustrates components linked to fluorescence for raw spectra obtained during step B) by application of the method according to the invention on a barley sample (in a solid line) and by fluorescence spectroscopy by the reference method known from the prior art (in a dotted line) for an excitation wavelength of 340 nm, FIG. 6b corresponds to the spectra of FIG. 6a after Gaussian filtering.

In reference to FIG. 6a, the raw spectrum obtained during step B) by application of the method according to the invention (in a solid line) is compared with the raw spectrum obtained by fluorescence spectroscopy by means of the reference method known from the prior art (in a dotted line). The sample that this relates to is barley and is presented in the form of grains. The excitation wavelength used for taking these measurements has been fixed at 340 nm. As can be seen in FIG. 6a, the signal/noise ratio of the raw spectrum obtained by the reference method is obviously less significant than in the raw spectrum obtained during step B) by application of the method according to the invention.

Figure 6B:
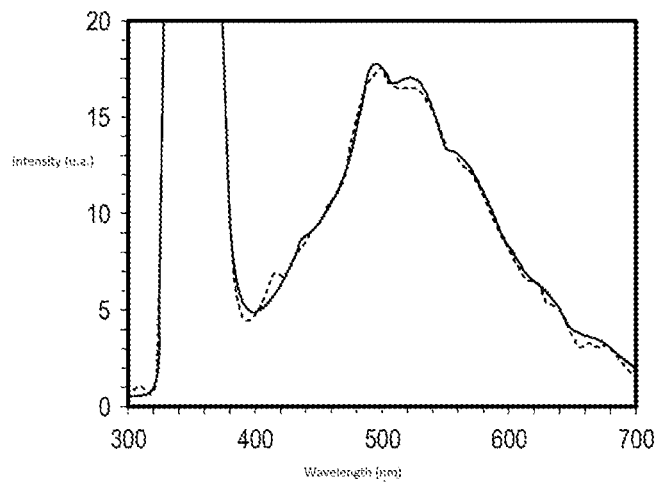
FIG. 6c illustrates a series of spectra obtained during step B) by repetition of the method according to the invention on one same barley sample for an excitation wavelength of 340 nm.
FIG. 6d illustrates a series of spectra obtained by fluorescence spectroscopy by the reference method known from the prior art on one same barley sample for an excitation wavelength of 340 nm.
FIG. 6e illustrates the residue from each of the spectra of FIG. 6c with respect to the average spectrum.
FIG. 6f illustrates the residue from each of the spectra of FIG. 6d with respect to the average spectrum.

FIG. 6b shows the result of the application of a Gaussian-type digital filter, the aim of which is to filter the electronic noise present in the signal on the raw spectrum obtained during step B) by application of the method according to the invention (in a solid line) and on the raw spectrum obtained by fluorescence spectroscopy by means of the reference method known from the prior art (in a dotted line).

Figure 6C:
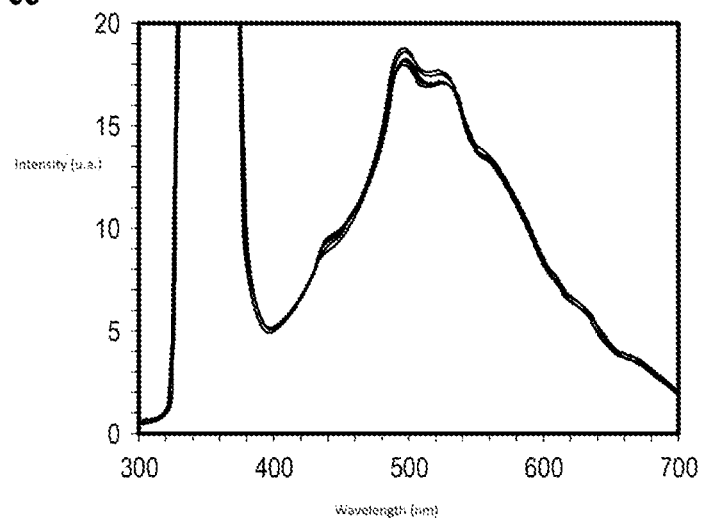
Figure 6D:
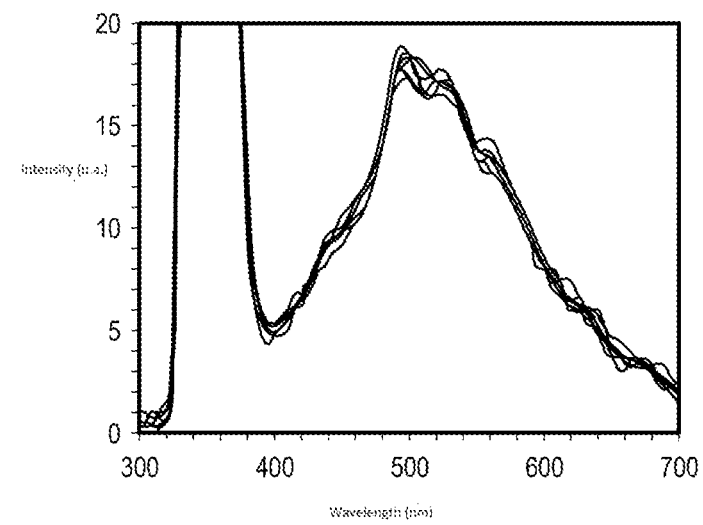

Moreover, FIG. 6c shows the excellent repeatability of the fluorescence measurements taken during the implementation of the method according to the invention on the same sample. It is obviously better than the repeatability which can be obtained by taking the same measurements with the reference method (FIG. 6d) and this, despite the prior application of a digital filter. The very obvious superiority of the repeatability of the measurements is explained by the optimisation, at the level of the acquisition, of the signal/noise ratio of the spectra on all the spectral components that the implementation of the method according to the invention allows.

Figure 6E:
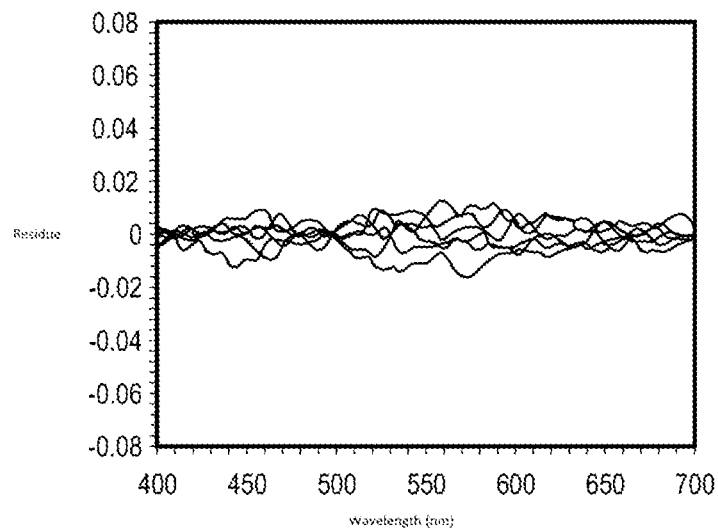
Figure 6F:
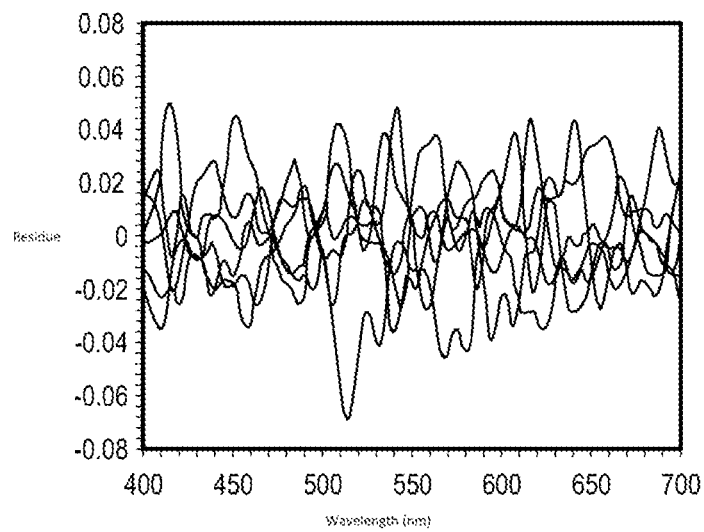
Figure 7A:
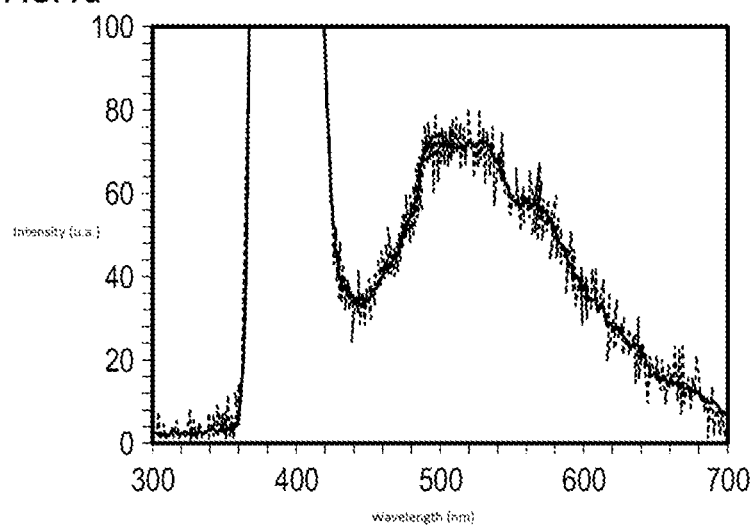
FIG. 7a illustrates components linked to fluorescence for raw spectra obtained during step B) by application of the method according to the invention on a barley sample (in a solid line) and by fluorescence spectroscopy by the reference method known from the prior art (in a dotted line) for an excitation wavelength of 385 nm, FIG. 7b corresponds to the spectra of FIG. 7a after Gaussian filtering.
Figure 7B:
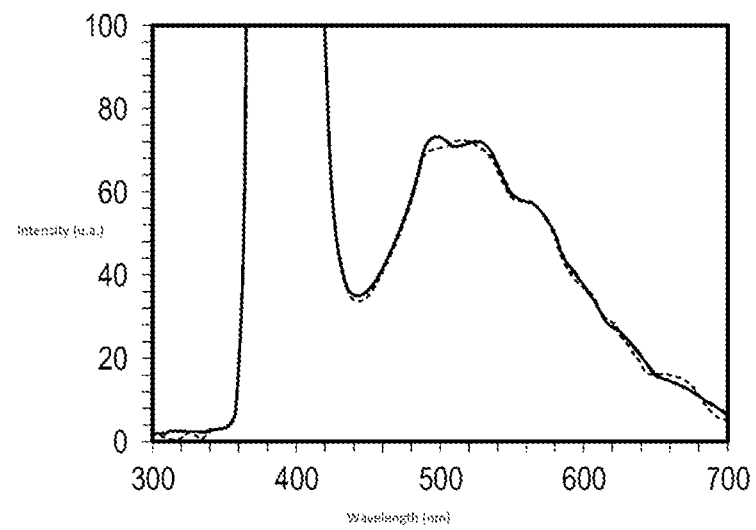
FIG. 7c illustrates a series of spectra obtained during step B) by repetition of the method according to the invention on one same barley sample for an excitation wavelength of 385 nm.
FIG. 7d illustrates a series of spectra obtained by fluorescence spectroscopy by the reference method known from the prior art on one same barely sample for an excitation wavelength of 385 nm.
FIG. 7e illustrates residue from each of the spectra of FIG. 7c with respect to the average spectrum.
FIG. 7f illustrates residue from each of the spectra of FIG. 7d with respect to the average spectrum.
Figure 7C:
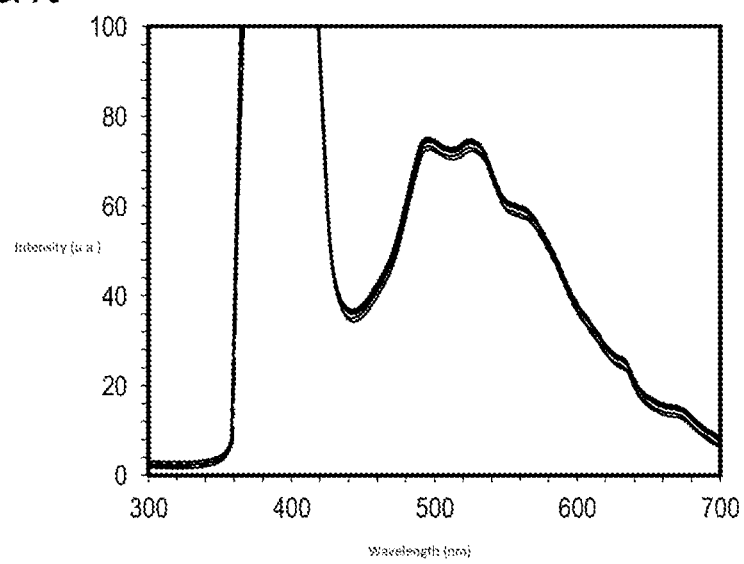
Figure 7D:
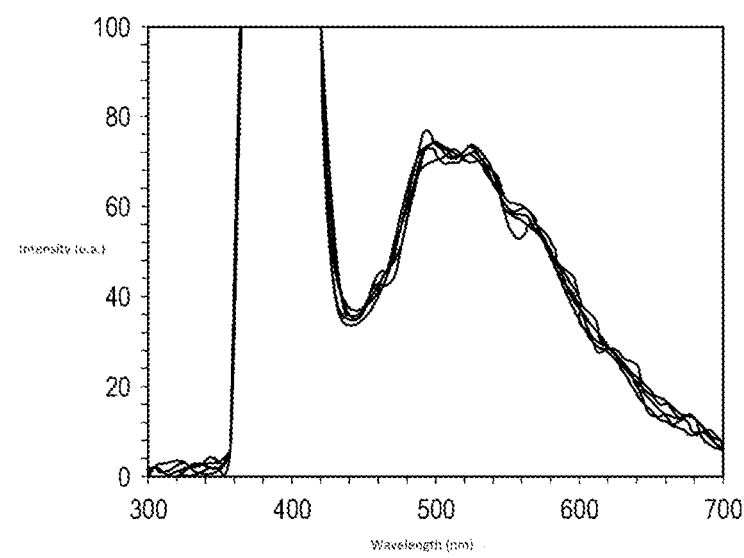
Figure 7E:
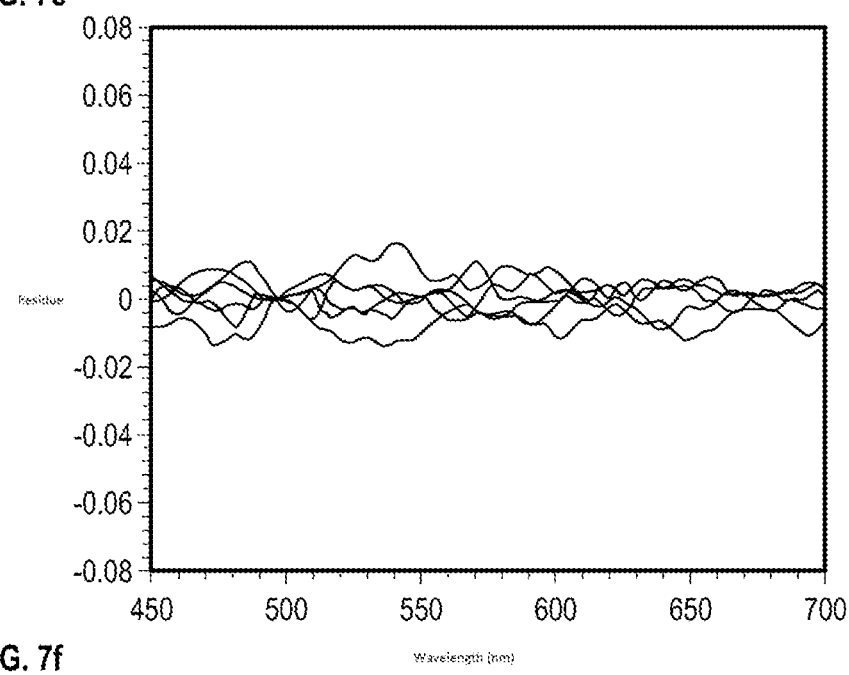
Figure 7F:
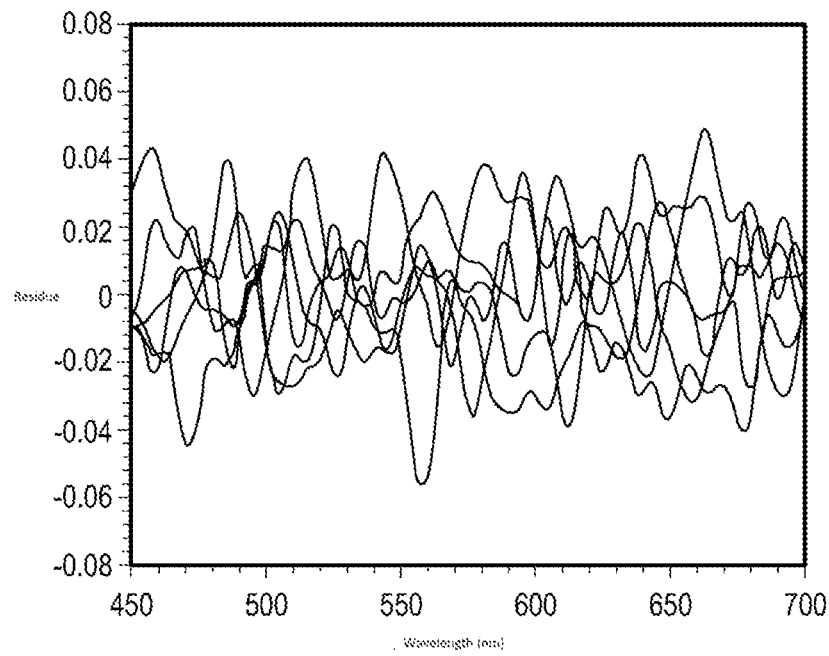

In FIGS. 6e and 6f, it can be seen that this induces significant differences on the residue measured with respect to the average spectrum according to the method implemented. By applying the method of the invention on the one hand, there is less variation of residue and on the other hand, there is less staggering between the residue of each repetition.

In reference to FIGS. 7a to 7f, it can be seen that the same conclusions are applied when the excitation wavelength is 385 nm.

Figure 8A:
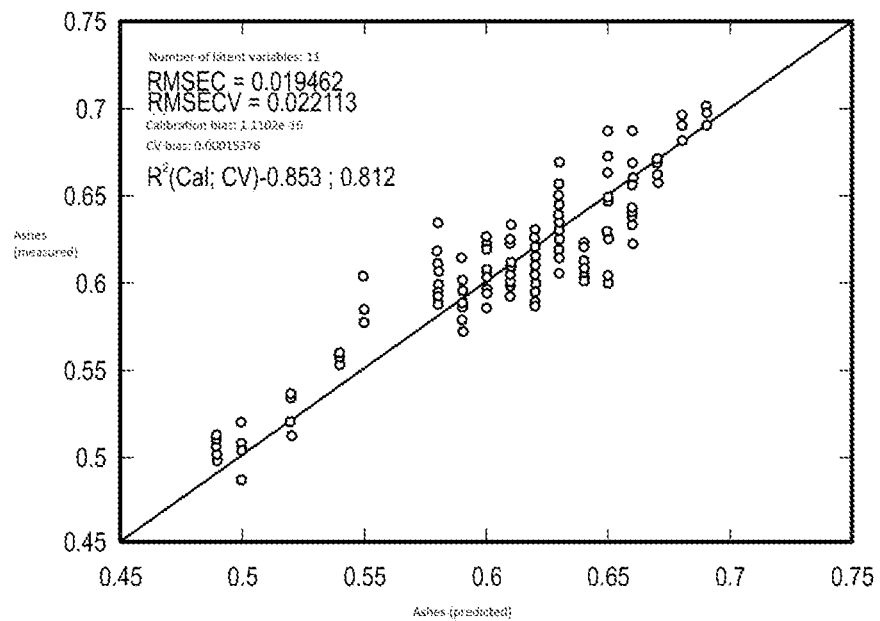
FIG. 8a illustrates a PLS regression (RMSECV=0.022%) obtained by connecting the values measured by infrared spectroscopy by the reference method known from the prior art (abscissa axis) and the predicted values by cross-validation (ordinate axis) for each sample of a batch of 204 flours.
Figure 8B:
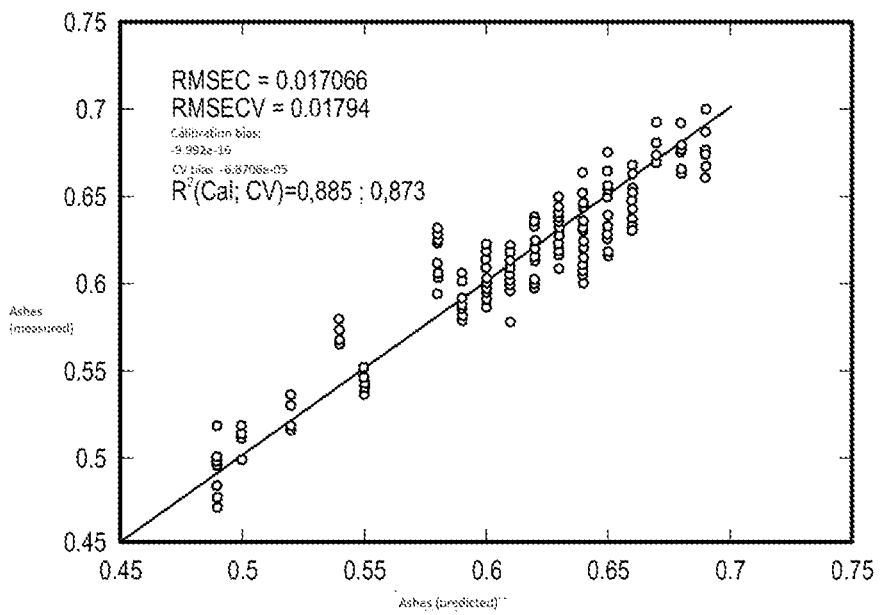
FIG. 8b illustrates an MLR regression (RMSECV=0.018%) obtained by connecting the values measured by fluorescence spectroscopy by the reference method known from the prior art (abscissa axis) and the predicted values by cross-validation (ordinate axis) for each sample of a batch of 204 flours.
Figure 9:
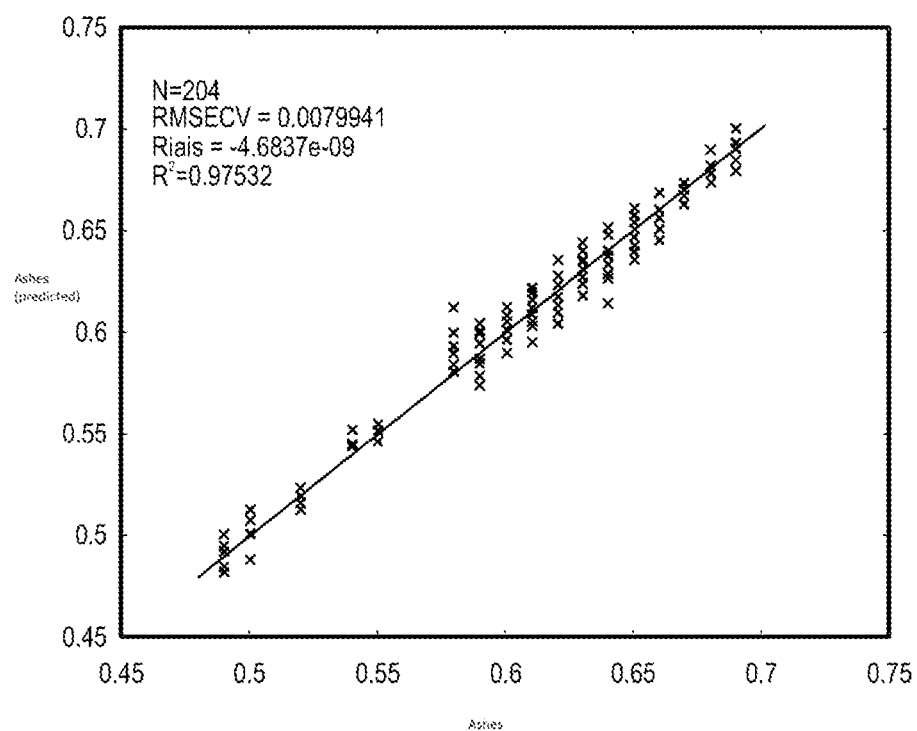
FIG. 9 illustrates a successive PLS regression (RMSECV=0.008%) achieved by jointly using the values measured by infrared spectroscopy and fluorescence spectroscopy (abscissa axis) according to the method of the invention of ashes on wheat flour and the predicted values by cross-validation (ordinate axis) for each sample of a batch of 204 flours in order to construct a calibration.

The table below presents, as a summary, the results illustrated in FIGS. 8a, 8b and 9. In FIGS. 8a and 8b, the 204 flour samples have been measured on the same appliance, on the one hand with the infrared module, and on the other hand with the fluorescence module (separately as in the prior art). The figures below show the calibration regressions obtained by connecting, in the abscissa, the values measured by the reference method for each sample and, in the ordinate, the predicted values in cross-validation from the regression by the least squares in infrared fluorescence or the multiple linear regression in fluorescence spectroscopy, the latter being itself constructed from PARAFAC breakdown scores.

TABLE 1

|  | Infrared spectroscopy measurements (FIG. 8a) | Fluorescence spectroscopy measurements (FIG. 8b) | Single chamber measurements by IR and Fluo spectroscopy according to the invention (FIG. 9) |
| --- | --- | --- | --- |
| Calibration (RMSEC) | 0.020 | 0.017 | 0.005 |
| Cross-validation | 0.022 (RMSECV) | 0.018 (RMSECV) | 0.024 (RMSEP) |
| External validation (RMSEP) | 0.065 | 0.085 | 0.023 |

The abbreviation:

RMSEC means "root mean square error of calibration"

RMSEVC means "root mean square error of cross-validation", and

RMSEP means "root mean square error of prediction".

Table 1 shows an obvious improvement of the error of calibration, with a degradation in external prediction in the case of the two technologies taken separately, while the degradation is observed in cross-validation in the case of coupling. This can however be expressed by a slight over-modelling during calibration.

In any case, an improvement of more than 3 times the performance of the external predictions is observed, thanks to the coupling of the infrared spectroscopy and fluorescence spectroscopy measurements.

The embodiments shown in the mentioned figures are only possible examples, not at all limiting, of the invention which comprises, on the contrary, variants of embodiments and designs in the scope of a person skilled in the art.

The invention claimed is:

1. Device for analysing a heterogenous sample, said device comprising:
   a measurement module comprising:
      a reservoir configured to accommodate said sample and equipped with a first wall and a second wall opposite the first wall,
      a first infrared spectroscopy subassembly comprising a first excitation source configured to emit an electromagnetic radiation in the infrared and/or the near-infrared field to the first wall of the reservoir, said first wall being transparent for infrared electromagnetic radiation, and first means for acquiring transmittance spectra,
      a second fluorescence spectroscopy subassembly comprising at least one second excitation source configured to emit an electromagnetic radiation in the ultraviolet and/or visible field to the second wall of the reservoir, said second wall being transparent for the electromagnetic radiations, such that the a volume of the sample which is illuminable by the first excitation source corresponds at least partially to a volume of the sample which is illuminable by the second excitation source, and second means for acquiring fluorescence spectra of said sample, the first subassembly comprising a diffusing and transparent optical element for the electromagnetic radiation emitted by said first excitation source, said optical element being positioned between the first excitation source and the first wall of the reservoir or between the second wall of the reservoir and the first means for acquiring transmittance spectra, outside of an optical path of the electromagnetic radiation emitted by the second excitation source and outside of a solid angle for collecting a fluorescence signal emitted by the sample when the electromagnetic radiation emitted by the second excitation source is exposed, and a processing module connected to the measurement module by a communication network and comprising a processor configured to analyse data obtained by infrared spectroscopy and fluorescence spectroscopy.

2. Device according to claim 1, wherein the optical element comprises the first wall of said reservoir.

3. Device according to claim 1, wherein the first wall of the reservoir is movable along an axis orthogonal to a plane passing through the first wall.

4. Device according to claim 1, wherein the second wall of the reservoir is anti-reflective for the electromagnetic radiation emitted by the second source.

5. Device according to claim 1, wherein said second source is located between the second wall and the first means for acquiring transmittance spectra.

6. Device according to claim 1, wherein an axis passing through the second means for acquiring fluorescence spectra and a median plane and substantially orthogonal to the second wall of the reservoir forms an angle with respect to an axis passing through the first excitation source and the second means for acquiring fluorescence spectra.

7. Device according to claim 1, wherein the first excitation source emits a broadband polychromatic electromagnetic radiation, said first source consisting of a high-power halogen incandescence source.

8. Device according to claim 1, wherein the second excitation source emits a monochromatic electromagnetic radiation, said second source consisting of one or more LEDs.

9. Device according to claim 1, comprising a housing receiving a system for retaining the sample, said housing comprising inner faces on which the system for retaining the sample is flattened.

10. Device according to claim 9, the system for retaining the sample comprising:
  a) the reservoir, said reservoir comprising a first glazed part equipped with the first wall and a second glazed part equipped with the second wall, said first glazed part being removably mounted on said second glazed part,
  b) a support block comprising a connection portion and a base for positioning the system for retaining the sample forming a bend with the connection portion in the device,
  c) a removable portion comprising a housing receiving the reservoir, said second glazed part being fixed to the removable portion, said removable portion being removably connected with respect to the connection portion,
  d) an articulated portion comprising an opening, said articulated portion pivoting on the support block and capable of passing from a mounting position, wherein said articulated portion is away from the removable portion to a use position, wherein said articulated portion is folded down on the removable portion, said opening being opposite the reservoir, said articulated portion comprising compressible means allowing flattening of the system for retaining the sample against the inner faces of said housing of the module receiving the system for retaining the sample when said articulated portion is in the use position.

11. Method for analysing a heterogenous sample with a device according to claim 1, said method comprising the following steps:
  A) acquiring a transmittance spectrum of said sample with the first infrared spectroscopy subassembly,
  B) acquiring fluorescence spectra of said sample with the second fluorescence spectroscopy subassembly,
  C) analysing the data obtained by infrared spectroscopy and fluorescence spectroscopy by the processing module, a processor being configured to determine at least one criterion characterising said sample from data coming from the analysis,
  D) coupling the data obtained by infrared spectroscopy and fluorescence spectroscopy, at the spectral level, by the processing module, by concatenation of spectra, previously processed, and by association of scores coming from breakdown of each spectrum, for construct linear regressions or non-linear models and obtain calibrations of a descriptive criterion of a state of the sample, comprising technological, sensorial or nutritional and sanitary quality criterion.

* * * * *